United States Patent [19]
Koyama et al.

[11] Patent Number: 6,136,854
[45] Date of Patent: Oct. 24, 2000

[54] CYCLOPENTENONE DERIVATIVE

[75] Inventors: Nobuto Koyama; Katsushige Ikai; Eiji Kobayashi; Ikunoshin Kato, all of Otsu, Japan

[73] Assignee: Takara Shuzo Co., Kyoto, Japan

[21] Appl. No.: 09/359,069

[22] Filed: Jul. 21, 1999

Related U.S. Application Data

[63] Continuation of application No. PCT/JP98/00817, Feb. 26, 1998.

[30] Foreign Application Priority Data

Mar. 26, 1997 [JP] Japan ........................ 9-90011
Nov. 3, 1997 [JP] Japan ........................ 9-72855

[51] Int. Cl.$^7$ .................. A61K 31/235; C07C 69/76; C07C 69/52
[52] U.S. Cl. .................. 514/532; 514/533; 560/84; 560/193
[58] Field of Search .................. 560/84, 193; 514/532, 514/533

[56] References Cited

FOREIGN PATENT DOCUMENTS 2247151  2/1990  Japan .

OTHER PUBLICATIONS

Ahmad, T., On the formation of reductiv acid from pentoses or hexuronic acids Carbohydrates Res., vol. 247, pp. 217–222, 1993.

Amos B. Smith, "Stereocontrolled total synthesis of (.+−.)–pentenomycins. I–III, their epimers, and dehydropentenomycin I," *J. Organ. Chem.*, vol. 47, No. 10, pp. 1855–1869 (1982).

International Preliminary Examination Report for International Application No. PCT/JP98/00817, Feb. 25, 1999.

*Primary Examiner*—Gary Geist
*Assistant Examiner*—Leigh C. Maier
*Attorney, Agent, or Firm*—Kolisch Hartwell Dickinson McCormack & Heuser

[57] ABSTRACT

Cyclopentenone derivative having a structure of 5-($R_1$COO—)-4-($R_2$COO—)—substituted 2-cyclopenten-1-one ($R_1$ and $R_2$ are some or different and each is alkyl group, alkenyl group or aryl group) or an optically active substance thereof; a method for the manufacture of the cyclopentenone derivative by the reaction of 4,5-dihydroxy-2-cyclopenten-1-one with the corresponding carboxylic acid or a reactive derivative thereof; and anticancer agent, apoptosis-inducing agent and antibacterial agent containing said derivative.

9 Claims, 15 Drawing Sheets

CYCLOPENTENONE DERIVATIVE

This application is a continuation of PCT/JP98/00817, filed Feb. 26, 1998.

TECHNICAL FIELD

The present invention relates to the cyclopentenone derivative useful in the field of pharmaceutical agents having a physiological activity such as anticancer action and also relates to a method for the manufacture of said compounds.

PRIOR ART

Pharmaceutical agents which have been used in clinical therapy include many agents such as anticancer agents, antibiotic substances, immunipotentiators, immunomodulators, etc. (such as alkylating agents, antimetabolites and plant alkaloids) but it can be hardly said that such a drug therapy has been completely established already.

Among those agents, prostaglandin A and J having an α, β-unsaturated carbonyl in a five-membered ring among the prostaglandins derived from natural substances have been reported to have a possibility of being used as highly safe anticancer agents due to their inhibition of DNA synthesis and various derivatives of them have been synthesized (refer to the Japanese Laid-Open Patent Publication Sho-62/96438).

PROBLEMS TO BE SOLVED BY THE INVENTION

An object of the present invention is to develop the cyclopentenone derivative having a physiological action such as anticancer action, apoptosis-inducing action, antibacterial action, etc. and to offer a method for the manufacture of said compounds and pharmaceutical agents containing said compounds.

MEANS TO SOLVE THE PROBLEMS

The present inventors have conducted an intensive study for achieving said object and have found that the cyclopentenone derivative represented by the formula [II] is produced by the reaction of 4,5-dihydroxy-2-cyclopenten-1-one (hereinafter, referred to as just "cyclopentenone") represented by the formula [III] with carboxylic acid and/or a reactive derivative thereof and that said cyclopentenone derivative of the present invention has various strong physiological activity such as cell growth inhibiting activity on cancer cells, etc. whereby the present invention has been achieved.

The present invention will be summarized to be as follows. Thus, the first feature of the present invention relates to a cyclopentenone derivative represented by the following formula [I] or an optically active substance or a salt thereof.

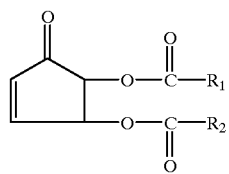
[I]

(In the formula, $R_1$ and $R_2$ are same or different and each of them is straight or branched alkyl group, straight or branched alkenyl group, aromatic group or aromatic-aliphatic group with a proviso that the case where $R_1=R_2=$—$CH_3$ is excluded.)

The second feature of the present invention relates to a method for the manufacture of a cyclopentenone derivative represented by the formula [II], characterized in that, 4,5-dihydroxy-2-cyclopenten-1-one represented by the following formula [III] and/or an optically active derivative thereof are/is made to react with a carboxylic acid and/or a reactive derivative thereof corresponding to $R_3$ and $R_4$ of the cyclopentenone derivative represented by the following formula [II] either simultaneously or successively.

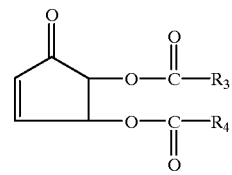
[II]

(In the formula, $R_3$ and $R_4$ are same or different and each of them is straight or branched alkyl group, straight or branched alkenyl group, aromatic group or aromatic-aliphatic group.)

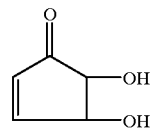
[III]

The third feature of the present invention is a pharmaceutical agent which is characterized in containing the compound selected from the cyclopentenone derivative, and optically active substance or a salt thereof of the first feature of the present invention as an effective component.

The fourth feature of the present invention is a pharmaceutical agent which is characterized in containing compound selected from cyclopentenone derivative, an optically active substance or a salt thereof obtained by the method of the second feature of the present invention as an effective component.

In a preferred embodiment of the third and fourth features of the present invention, said pharmaceutical agent is an anticancer agent, apoptosis inducer or antibacterial agent.

EMBODIMENTS OF THE INVENTION

Figure 1:
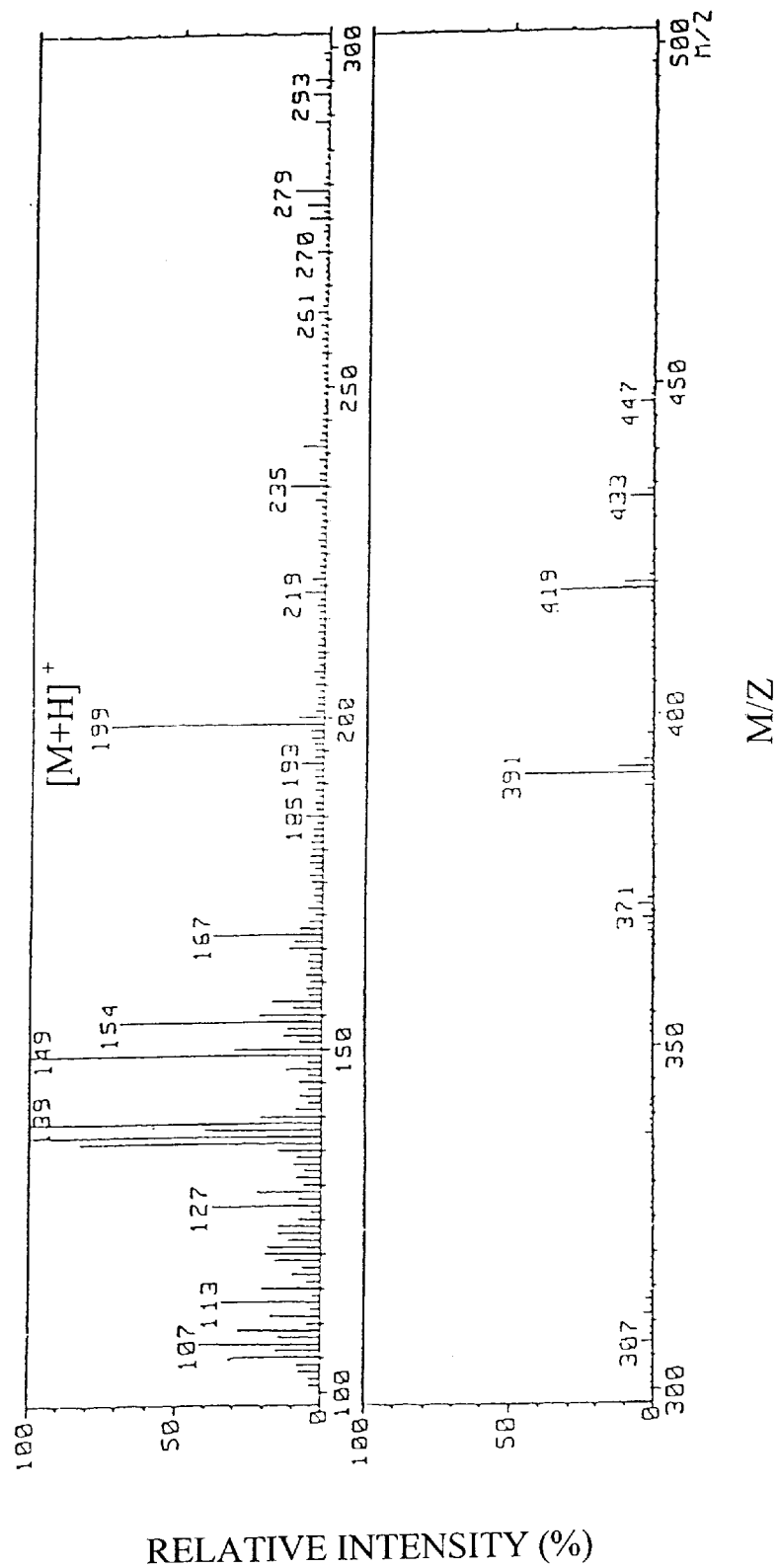
FIG. 1 shows a mass spectrum of diacetylcyclopentenone.

The present invention will now be specifically illustrated hereinafter.

The cyclopentenone represented by the formula [III] used in the present invention covers both isomers where the configurations of hydroxyl groups at 4- and 5-positions are cis and trans. In the present invention, any of cis-cyclopentenone, trans-cyclopentenone and a mixture of cis- and trans-cyclopentenone may be used. It is also possible to use optically active substances thereof.

cis-Cyclopentenone may be prepared by a chemical synthesis [Helvetica Chimica Acta, volume 55, pages 2838–2844 (1972)]. trans-Cyclopentenone may be prepared either by a chemical synthesis [Carbonhydrate Res., volume 247, pages 217–222 (1993)] or by heating uronic acid such as glucuronic acid, uronic acid derivative such as glucuronolactone, etc. (refer to PCT/JP97/03052). In the present invention, it is also possible to use such a heated product or partially purified product or purified product thereof.

For example, when D-glucuronic acid is used as a uronic acid and its 1% solution is heated at 121° C. for four hours, the cyclopentenone is produced in the heat-treated substance. The cyclopentenone in this heat-treated substance is extracted with a solvent and the extract is concentrated. Then, this concentrated extract is separated by means of a silica gel column chromatography, the eluted cyclopentenone fraction is concentrated, the cyclopentenone is extracted with chloroform from the concentrate and the extract of the concentrate is subjected to a normal phase column chromatography whereupon the cyclopentenone in the heat-treated substance is isolated.

Physical property of the cyclopentenone will be given as hereunder. Incidentally, a mass spectrometric analysis of the cyclopentenone was conducted using a mass spectrometer DX302 (manufactured by Nippon Denshi). Further, measurement of an NMR using heavy chloroform as a solvent was conducted by JNM-A 500 (manufactured by Nippon Denshi). Specific rotation was measured by a DIP-370 polarimeter (manufactured by Nippon Bunko); ultraviolet absorption spectrum was measured by a UV-2500 spectrophotometer (manufactured by Shimadzu); and infrared absorption spectrum (IR) was measured by an FTIR-8000 infrared spectrophotometer (manufactured by Shimadzu).

MS m/z 115 [M+H]$^+$ $^1$H-NMR (CDCl$_3$): δ4.20 (1H, d, J=2.4 Hz, 5-H), 4.83 (1H,m, 4-H), 6.30 (1H, dd, J=1.2, 6.1 Hz, 2-H), 7.48 (1H, dd, J=2.1, 6.1 Hz, 3-H).

Incidentally, the chemical shift value of the $^1$H-NMR was given on a basis that the chemical shift value of CHCl$_3$ was 7.26 ppm.

Optical rotation: [α]D$^{20}$ 0° (c 1.3, water)

UV: λ$_{max}$ 215 nm (water)

IR (KBr method): absorptions were noted at 3400, 1715, 1630, 1115, 1060, 1025 cm$^{-1}$.

When the isolated cyclopentenone is subjected to an optical resolution, (−)-4,5-dihydroxy-2-cyclopenten-1-one and (+)-4,5-dihydroxy-2-cyclopenten-1-one are obtained. It goes without saying that the cyclopentenone obtained by a synthetic method can be subjected to an optical resolution as well.

For example, the cyclopentenone is dissolved in ethanol. To this ethanolic solution is further added hexane/ethanol (94/6) to prepare a cyclopentenone solution. The cyclopentenone can be optically resolved when this sample solution is subjected to an HPLC using, for example, a Chiral Pack AS (manufactured by Daicel Chemical Industries) under such a condition that the column temperature was 40° C. and the mobile phase was hexane/ethanol (94/6).

Optical rotation of the optically resolved (−)-trans-4,5-dihydroxy-2-cyclopenten-1-one [hereinafter, referred to as (−)-cyclopentenone] is [α]$_D$$^{20}$−150° (c 0.30, ethanol) while that of the optically resolved (+)-trans-4,5-dihydroxy-2-cyclopenten-1-one [hereinafter, referred to as (+)-cyclopentenone] is [α]$_D$$^{20}$+104° (c 0.53, ethanol). Incidentally, the optical rotation was measured by the above-mentioned polarimeter of the type DIP-370 (manufactured by Nippon Bunko).

After that, each of (−)-cyclopentenone and (+)-cyclopentenone was subjected to structural analysis by means of mass analysis and nuclear magnetic resonance (NMR), measurement of UV absorption spectrum and measurement of infrared absorption spectrum by the method mentioned already. As a result, both optically active substances showed the same result as that of the cyclopentenone before the optical resolution.

Each of the optically resolved (−)-cyclopentenone and (+)-cyclopentenone was converted to a p-dimethylaminobenzoyl derivative, the circular dichroism spectrum (CD) was measured using a circular dichroism while the abscissa indicates wave length (nm). Incidentally, the above stereostructure is given hereunder as the formula [IV]

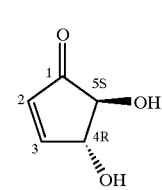

[IV]

Figure 15:
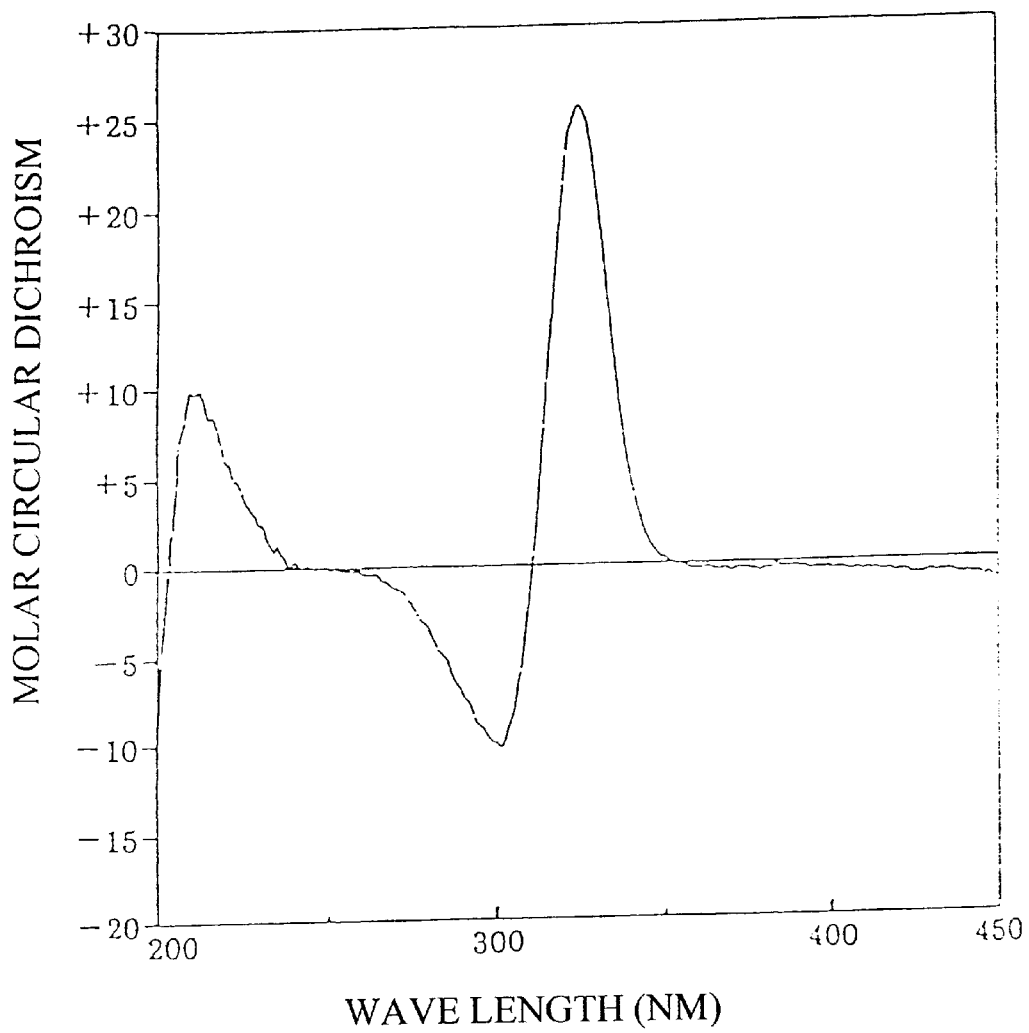
FIG. 15 shows a CD of p-dimethylaminobenzoyl derivative of (+)-cyclopentenone and a stereostructure of (+)-cyclopentenone.
Figure 15:
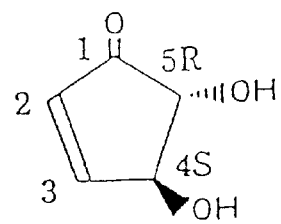

CD of p-dimethylaminobenzoyl derivative of (+)-cyclopentenone and stereostructure of (+)-cyclopentenone are shown in FIG. 15. In the drawing, the ordinate indicates molar circular dichroism while the abscissa indicates wave length (nm). Incidentally, the above stereostructure is given hereunder as the formula [V]

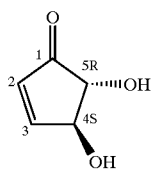

[V]

Figure 14:
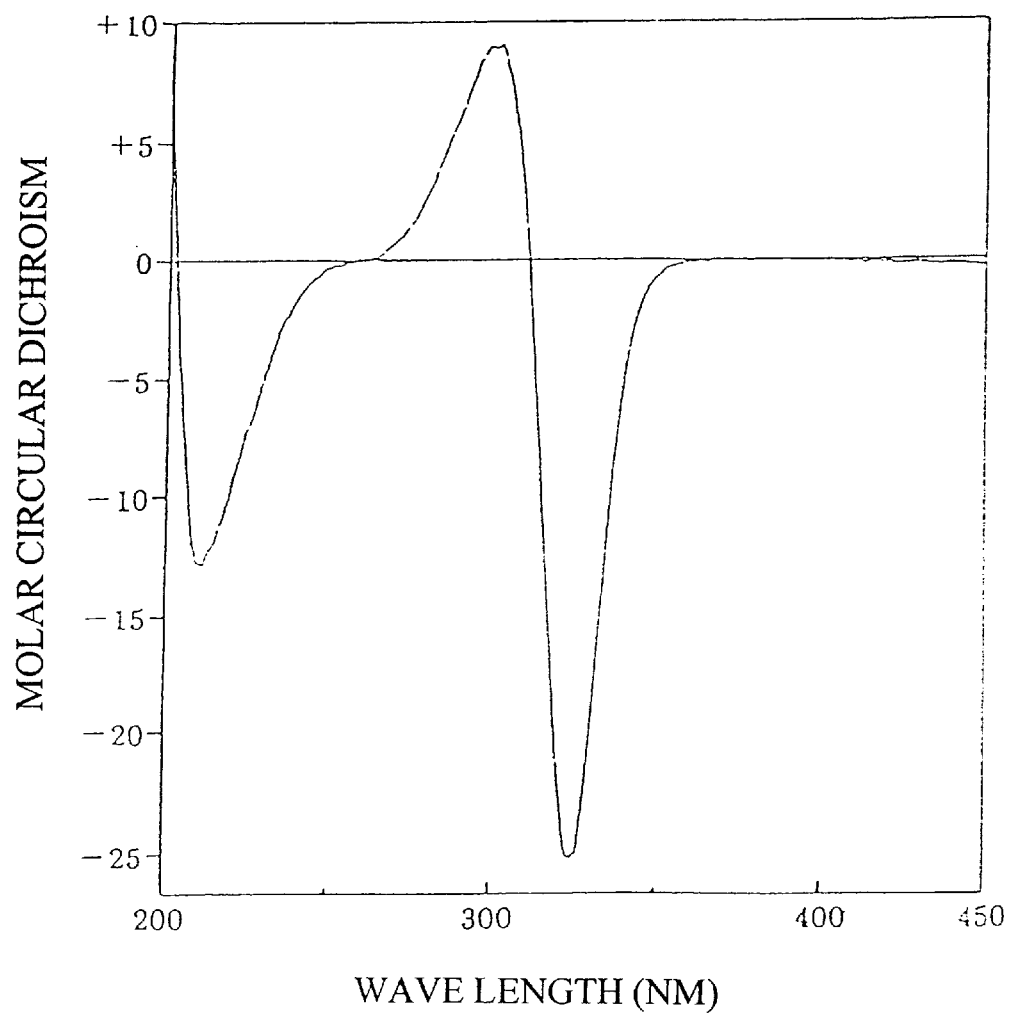
FIG. 14 shows a CD of p-dimethylaminobenzoyl derivative of (−)-cyclopentenone and a stereostructure of (−)-cyclopentenone.
Figure 14:
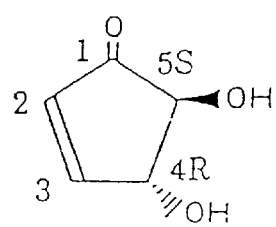

As shown in FIG. 14, FIG. 15, formula [IV]and formula [V], the (−)-cyclopentenone is (−)-(4R, 5S)-trans-4,5-dihydroxy-2-cyclopenten-1-one while the (+)-cyclopentenone is (+)-(4S, 5R)-trans-4,5-dihydroxy-2-cyclopenten-1-one.

The above-mentioned cyclopentenones or an optically active substance thereof may be manufactured by any method, i.e. they may be manufactured by a method disclosed in this specification or by means of chemical synthesis; and trans- and cis-cyclopentenone, a mixture thereof or optically active substances thereof may be used in the present invention as well.

When the cyclopentenone and/or an optically active substance thereof are/is made to react with a carboxylic acid and/or a reactive derivative thereof having straight or branched alkyl group, straight or branched alkenyl group, aromatic group or aromatic aliphatic group either simultaneously or successively, the cyclopentenone derivative of the present invention represented by the formula [II] or an optically active substance derivative thereof is produced in the reaction solution.

A carboxylic acid having straight or branched alkyl group may be used as the carboxylic acid having alkyl group and the length of the alkyl chain can be appropriately selected according to the biological activity, solubility, etc. of the cyclopentenone derivative.

Examples of the applicable carboxylic acid having straight alkyl group are acetic acid, propionic acid, butyric acid, valeric acid, hexanoic acid, heptanoic acid, n-octanoic acid, pelargonic acid, n-decanoic acid, undecanoic acid, lauric acid, tridecanoic acid, myristic acid, pentadecanoic acid, palmitic acid, heptadecanoic acid, stearic acid, nonadecanoic acid, icosanoic acid, hehenic acid, lignoceric acid, cerotic acid and melissic acid.

Examples of the applicable carboxylic acid having branched alkyl group are isobutyric acid, isovaleric acid, 2-methylbutyric acid, pivalic acid, 4-methylvaleric acid and 1,2-dimethylvaleric acid.

With regard to the carboxylic acid having alkenyl group, a carboxylic acid having straight or branched alkenyl group may be used and the chain length, degree of unsaturation and position of the unsaturated bond of the alkenyl group may be appropriately selected according to biological activity, solubility, etc. of the cyclopentenone derivative.

Examples of the applicable carboxylic acid having straight alkenyl group are acrylic acid, vinylacetic acid, crotonic acid, isocrotonic acid, allylacetic acid, 2-hexenoic acid, 3-hexenoic acid, 3-octenoic acid, obtusilic acid, 10-undecenoic acid, palmitoleic acid, petroselinic acid, elaidic acid, oleic acid, linoleic acid, α-linolenic acid, γ-linolenic acid, eleostearic acid, icosatrienoic acid, arachidoonic acid, eicosapentaenoic acid, brassidic acid, erucic acid, docosahexaenoic acid, ximenic acid and 21-triacontenoic acid.

Examples of the applicable carboxylic acid having aromatic group are benzoic acid, toluic acid, chlorobenzoic acid, bromobenzoic acid, nitrobenzoic acid, phthalic acid, acetylsalicylic acid, acetylsalicylsalicylic acid, aminosalicylic acid, p-hydroxybenzoic acid, vanillic acid, orsellinic acid, naphthoic acid, cinchomeronic acid, xanthurenic acid, quininic acid and kynurenic acid and a carboxylic acid having appropriate aryl group may be selected according to biological activity, solubility, etc. of the cyclopentenone derivative to be manufactured.

Examples of the applicable carboxylic acid having aromatic aliphatic group are phenylacetic acid, phenylpropionic acid, phenyllactic acid, phenylpyruvic acid, cinnamic acid, atropic acid and naphthylacetic acid and a carboxylic acid having appropriate aralkyl group may be selected according to biological activity, solubility, etc. of the cyclopentenone derivative to be manufactured.

Examples of the reactive derivative of the carboxylic acid used in the present invention are acid halides, acid anhydrides, acid esters and salts and a reactive derivative of carboxylic acid to be used may be manufactured depending upon the object.

Reaction of the carboxylic acid or a reactive derivative thereof with the cyclopentenone may be conducted in such a manner that $R_3$ and $R_4$ of the cyclopentenone derivative become either same or different. Thus, carboxylic acids having different $R_3$ and $R_4$ may be made to react with the cyclopentenone either simultaneously or successively. When one of the hydroxyl groups of the cyclopentenone is protected at that time, it is possible to efficiently manufacture the cyclopentenone derivative having different $R_3$ and $R_4$.

The cyclopentenone derivative or an optically active substance thereof which is produced by the reaction of the cyclopentenone or an optionally active substance thereof with carboxylic acid has a potent inhibiting activity for growth of oncogene and can be purified and isolated from the reaction solution using said activity as an index. The means for purification and isolation may be known purifying means such as chemical method and physical method. Thus, conventionally known methods such as gel filtration, fractionation using a molecular weight fractionating membrane, extraction with solvent, fractional distillation and various chromatographic methods using ion exchange resin, etc. are combined whereby the cyclopetenone derivative or an optically active substance thereof can be purified and isolated.

For example, the cyclopentenone or an optically active substance thereof, 4-methylaminopyridine and carboxylic acid are dissolved in dichloromethane, then N,N-dichyclohexylcarbodiimide is added thereto with ice cooling and the mixture is subjected to the reaction whereupon the cyclopentenone derivative of the present invention is produced. The resulting product is purified by means of a silica gel thin layer chromatography to isolate the desired cyclopentenone derivative.

It is also possible that the cyclopentenone or an optically active substance thereof is made to react with acetic anhydride in anhydrous pyridine and the resulting diacetylcyclopentenone is purified and isolated from the reaction mixture.

Separation of the optically active substance of the cyclopentenone derivative obtained by the present invention can be conducted by subjecting the racemic mixture to mechanical resolution, preferential crystallization, resolution by crystallization as diastereomer salts or as inclusion compounds, dynamic resolution using enzymes or microorganism, resolution by means of chromatography, etc.

Gas chromatography, liquid chromatography, thin layer chromatography, etc. may be used in the case of a resolution by chromatography and a chiral stationary phase which is suitable for each of them may be used.

A method using a chiral stationary phase, a method using a chiral eluate, separation as a diastereomer, etc. may be used in an optical resolution by liquid chromatography.

A stationary phase of an amide type, that of a urea type, that of a ligand exchange type, polysaccharide-polysaccharide derivative stationary phase, protein stationary phase, polymethacrylate stationary phase, polymethacrylamide stationary phase, etc. may be used as a chiral stationary phase.

With regard to an eluting liquid, that of a hexane type, an alcohol type, an aqueous (buffer) type, etc. may be suitably used taking the combination with the above-mentioned stationary phase into consideration.

With regard to the salt of the compound of the present invention or optically active substance thereof, salts which are acceptable as pharmaceutical agents are exemplified and they may be prepared by converting by means of known methods.

The cyclopentenone derivative, an optically active substance thereof or a salt thereof obtained by the present invention has a cell growth suppressing action to cancer cells such as human promyelocytic leukemia cells HL-60, human acute lymphoblastic leukemia cells MOLT-3, pulmonary cancer cells A-549, SV40-transformed pulmonary cancer cells WI-38VA13, hepatoma cells Hep G2, colon cancer cells HCT 116, human colon cancer cells SW 480, human colon cancer cells WiDr, stomach cancer cells AGS and myeloma cells. The pharmaceutical agent containing the compound selected from cyclopentenone derivative of the present invention, an optically active substance or a salt thereof as an effective component can be prepared, i.e. when the compound selected from the cyclopentenone derivative of the present invention, an optically active substance thereof or a salt thereof is used as an effective component and is made into a pharmaceutical preparation by compounding with known pharmaceutical carriers, it is now possible to prepare an anticancer agent. Mechanism of the cell growth inhibiting activity on cancer cell of the cyclopentenone derivative, an optically active substance thereof or a salt thereof obtained by the present invention does not limit the scope of the present invention at all and, for example, an apoptosis inducing action to cancer cells is covered by the present invention as well.

Generally, the compound selected from the cyclopentenone derivative, an optically active substance thereof or a salt thereof is compounded with a pharmaceutically acceptable liquid or solid carrier and, if necessary, solvent, dispersing agent, emulsifier, buffer, stabilizer, filler, binder, disintegrating agent, lubricant, etc. are added thereto to give an anticancer agent which may be in solid such as tablets, granules, diluted powders, powders, capsules, etc. or in liquid such as solutions, suspensions, emulsions, etc. Further, this may be in a dry preparation which can be made into liquid by adding an appropriate carrier before use.

The pharmaceutical carrier may be selected depending upon the above-mentioned mode of the administration and form of the preparation. In the case of oral preparations, starch, lactose, sugar, mannitol, carboxymethyl cellulose, corn starch, inorganic salts, etc. may be used. In the manufacture of oral preparations, binders, disintegrating agents, surface-active agents, lubricants, fluidity promoters, taste-correctives, coloring agents, flavors, etc. may be further compounded therewith.

On the other hand, in the case of parenteral preparations, they may be prepared by common methods where the compound selected from the cyclopentenone derivative, an optically active substance thereof or a salt thereof which is an effective ingredient of the present invention is dissolved or suspended in a diluent such as distilled water for injection, physiological saline solution, aqueous solution of glucose, vegetable oil for injection, sesame oil, peanut oil, soybean oil, corn oil, propylene glycol, polyethylene glycol, etc. followed, if necessary, by adding bactericides, stabilizers, isotonic agents, analgesics, etc. thereto.

The anticancer agent of the present invention is administered by an appropriate route depending upon the form of the preparation. There is no particular limitation for the method of administration as well and it may be administered by means of oral use, external use and injection. Injection preparations are administered, for example, intravenously, intramuscularly, subcutaneously, intracutaneously, etc. while preparations for external use include suppositories, etc.

Dose as an anticancer agent is appropriately decided by its form of preparation, method of administration, purpose of use and age, body weight and symptom of the patient to be treated and it is not constant but, usually, the amount of the cyclopentenone derivative, an optically active substance thereof or a salt thereof contained in the preparation is from 0.1 µg to 200 mg/kg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

The cyclopentenone derivative, an optically active substance or a salt thereof obtained by the present invention has an apoptosis inducing action and an apoptosis inducer containing at least one compound selected from the above as an effective component can be prepared. The apoptosis inducer can be made into pharmaceutical preparations according to the above-mentioned anticancer agent and is administered by the same manner as in the case of the anticancer agent.

The dose as the apoptosis inducers is not particularly specified but may be appropriately determined depending upon the dosage form, administration method, purpose of the use and age, body weight, conditions, etc. of the patient to whom the inducer is administered. Usually, however, the amount of the cyclopentenone derivative and/or an optically active substance thereof contained in the preparation for an adult is 0.1 µg-100 mg/kg per day. As a matter of course, the dose may vary depending upon various factors and, therefore, the dose less than the above-mentioned one may be sufficient in some cases while, in other cases, the dose more than the above may be necessary. The agent of the present invention may be administered orally as it is and, further, the agent may be taken daily after adding to common food and/or beverage as well.

Unlike necrosis which is a pathogenic death of cells, apoptosis is believed to be a death which is initially programmed in the gene of the cell itself. Thus, the gene which programs the apoptosis is activated by certain external or internal causes whereby programmed cell death gene protein is produced based upon said gene and then the cell itself is decomposed and dead by the resulting programmed death protein.

The apoptosis inducer of the present invention is quite useful since it is capable of induction of such apoptosis in desired tissues and cells and able to exclude the unnecessary cells or the pathogenic cells from living organisms in a natural state.

The apoptosis inducer of the present invention can be used in a method for the induction of apoptosis. Thus, when the cyclopentenone derivative, an optically active substance thereof or a salt thereof is used as an effective component, it is possible to induce apoptosis and said method is useful, for example, for elucidation of a mechanism for apoptosis induction and for screening of apoptosis inducers and apoptosis induction inhibitors.

The cyclopentenone derivative, an optically active substance or a salt thereof obtained by the present invention has an antibacterial activity and an antibacterial agent containing at least one compound selected from the above as an effective component can be prepared. The antibacterial agent can be made into pharmaceutical preparations according to the above-mentioned anticancer agent and is administered by an appropriate administration route depending upon the preparation form. There is no particular limitation for the method of administration as well and any of oral and external applications and injection may be applied. Injection may be administered, for example, intravenously, intramuscularly, subcutaneously and intracutaneously. External preparation includes suppository.

Does as an antibacterial agent is appropriately decided by its form of preparation, method of administration, purpose of use and age, body weight and symptom of the patient to be treated and it is not constant but, usually, the amount of the cyclopentenone derivative, an optically active substance thereof or a salt thereof contained in the preparation is from 10 μg to 20 mg/kg per day (for adults). Of course, the dose may vary depending upon various conditions and, therefore, the dose less than above may be sufficient in some cases while, in other cases, the does more than above may be necessary. The pharmaceutical agent of the present invention can be directly administered orally and, in addition, it can be added to any food and beverage so that the agent can be taken on a routine basis.

In addition, the antibacterial agent of the present invention may be used as an antiseptic agent for improving the preservability of food or beverage. It is further possible to add the cyclopentenone derivative, an optically active substance or a salt thereof to food or beverage and to use in an antiseptic method for food or beverage.

The antibacterial agent of the present invention is effective for both Gram-positive and Gram-negative bacteria. Furthermore, the antibacterial agent of the present invention has an antibacterial activity to bacteria for dental caries and those for periodontal disease and an intraoral preparations containing the antibacterial agent of the present invention can be offered. The form of the intraoral preparation may be a known one such as liquid or paste. An example of the intraoral preparation is a dentifrice. It is possible to offer antibacterial cosmetics using the antibacterial agent of the present invention. It is also possible to offer a bathing agent using the antibacterial agent of the present invention.

The cyclopentenone derivative, an optically active substance or a salt thereof obtained by the present invention can be efficiently manufactured from the cyclopentenone and a carboxylic acid or a reactive derivative thereof.

There is no particular limitation for the method of manufacturing the food and beverage containing the cyclopentenone derivative, an optically active substance or a salt thereof obtained by the present invention but cooking, processing and commonly-used manufacturing methods for food and beverage may be applied provided that an effective amount of the cyclopentenone derivative, an optically active substance or a salt thereof is contained in the resulting food or beverage.

The cyclopentenone derivative, an optically active substance or a salt thereof obtained by the present invention does not exhibit toxicity upon administration of its dose which is effective for achieving the physiological activity. For example, in the case of oral administration, no dead case was noted in mice by a single oral administration of 300 mg/kg of any of dipropionylcyclopentenone, dihexanoylcyclopentenone, di-2-hexenoylcyclopentenone and optically active substances and salts thereof.

To sum up, the cyclopentenone derivative, an optically active substance or a salt thereof obtained by the present invention can be easily manufactured and, due to its various physiological functions, it is a compound which is quite useful in broad area of pharmaceutical agents, foods, etc.

EXAMPLES

The present invention will be further illustrated by way of the following examples although the present invention is never limited to those examples. Incidentally, "%" used in the examples stands for "% by weight".

EXAMPLE 1

(1) D-Glucuroic acid (G 5269; manufactured by Sigma) (10 g) was dissolved in 1 liter of water, heated at 121° C. for four hours and concentrated in vacuo until about 10 ml. This was mixed with 40 ml of an upper layer of a 3:2:2 mixture of butyl acetate, acetic acid and water and centrifuged and the resulting supernatant liquid was concentrated in vacuo until about 10 ml.

The above extract was applied to silica gel (BW-300SP; 2×28 cm; manufactured by Fuji Silycia) for a column chromatography and separated using an upper layer of a 3:2:2 mixture of butyl acetate, acetic acid and water as an eluate at the flow rate of about 5 ml/minute under a pressure of 0.2 kg/cm$^2$ using a compressor. Fractionation was conducted to make a volume of one fraction 10 ml and a part of each fraction was analyzed by a thin layer chromatography whereupon cyclopentenone of a high purity was contained in 61st to 80th fractions. Those fractions were collected, concentrated in vacuo, extracted with 40 ml of chloroform and the extract was concentrated in vacuo to afford 100 mg of cyclopentenone.

The fraction was separated by means of a normal phase HPLC using a Palpack type S column (manufactured by Takara Shuzo) and, when a detection was conducted by an ultraviolet absorption of 215 nm, the purity was found to be 98%.

The above cyclopentenone (113.9 mg) was dissolved in 2.85 ml of ethanol. To this ethanolic solution was added 3.85 ml of hexane/ethanol (94/6) to prepare a cyclopentenone solution (17 mg/ml). This was filtered through a filter of 0.5 μm to prepare a sample solution for an optical resolution HPLC.

This sample solution was applied to an optical resolution HPLC, each of the fractions of the (−)-cyclopentenone in the earlier peak and the (+)-cyclopentenone in the later peak was collected and evaporated to dryness in vacuo to give 43.2 mg of the (−)-cyclopentenone and 43.0 mg of the (+)-cyclopentenone.

Conditions for Optical Resolution HPLC.

Columns; Chiral Pack AS (manufactured by Daicel) 2.0 cm×25.0 cm

Column temperature: 40° C.

Mobile phase: hexane/ethanol (94/6)

Flow rate: 14.0 ml/minute

Detection: UV 210 nm

Amount of the charged sample: 150 µl (2.55 mg)

Each of the (−)-cyclopentenone and (+)-cyclopentenone obtained herein contains about 1% of enantiomer and, therefore, they were subjected to an optical resolution under the above-mentioned conditions again. As a result, 19.7 mg of the (−)-cyclopentenone containing no enantiomer was obtained from 30.0 mg of the (−)-cyclopentenone of the earlier peak while, from 37.4 mg of the (+)-cyclopentenone of the later peak, 27.7 mg of the (+)-cyclopentenone containing no enantiomer was obtained. Incidentally, the eluting times in optical resolution HPLC of the (−)-cyclopentenone and (+)-cyclopentenone were 33 minutes and 40 minutes, respectively.

(2) To 29.6 mg of the cyclopentenone obtained by a method mentioned in Example 1-(1) were added 1 ml of anhydrous pyridine (295-26 manufactured by Nacalai Tesque) and 0.1 ml of acetic anhydride (002-26 manufactured by Nacalai Tesque) followed by stirring at room temperature for three hours. The reaction solution was extracted with chloroform to give 36 mg of diacetylcyclopentenone.

Mass analysis of the resulting diacetylcyclopentenone was conducted using a DX 302 mass spectrometer (manufactured by Nippon Denshi). In addition, it was dissolved in $CDCl_3$ and its structure was analyzed by means of NMR. JMN-A500 (manufactured by Nippon Denshi) was used as a nucleomagnetic resonance apparatus. The result will be given below. Incidentally, chemical shift values of $^1$H-NMR were expressed in such a manner that the chemical shift value of chloroform was 7.24 ppm.

MS m/z 199(M+H)$^+$ $^1$H-NMR

δ 2.12 (3H, S, —OCOCH$_3$), 2.16 (3H, S, —OCOCH$_3$), 5.16 (1H, d, J=3.0 Hz, H-5), 5.89 (1H, m, H-4), 6.40 (1H, d—d, J=1.5, 6.5 Hz, H-2), 7.43 (1H, d—d, J=2.5, 6.5 Hz, H-3)

Figure 2:
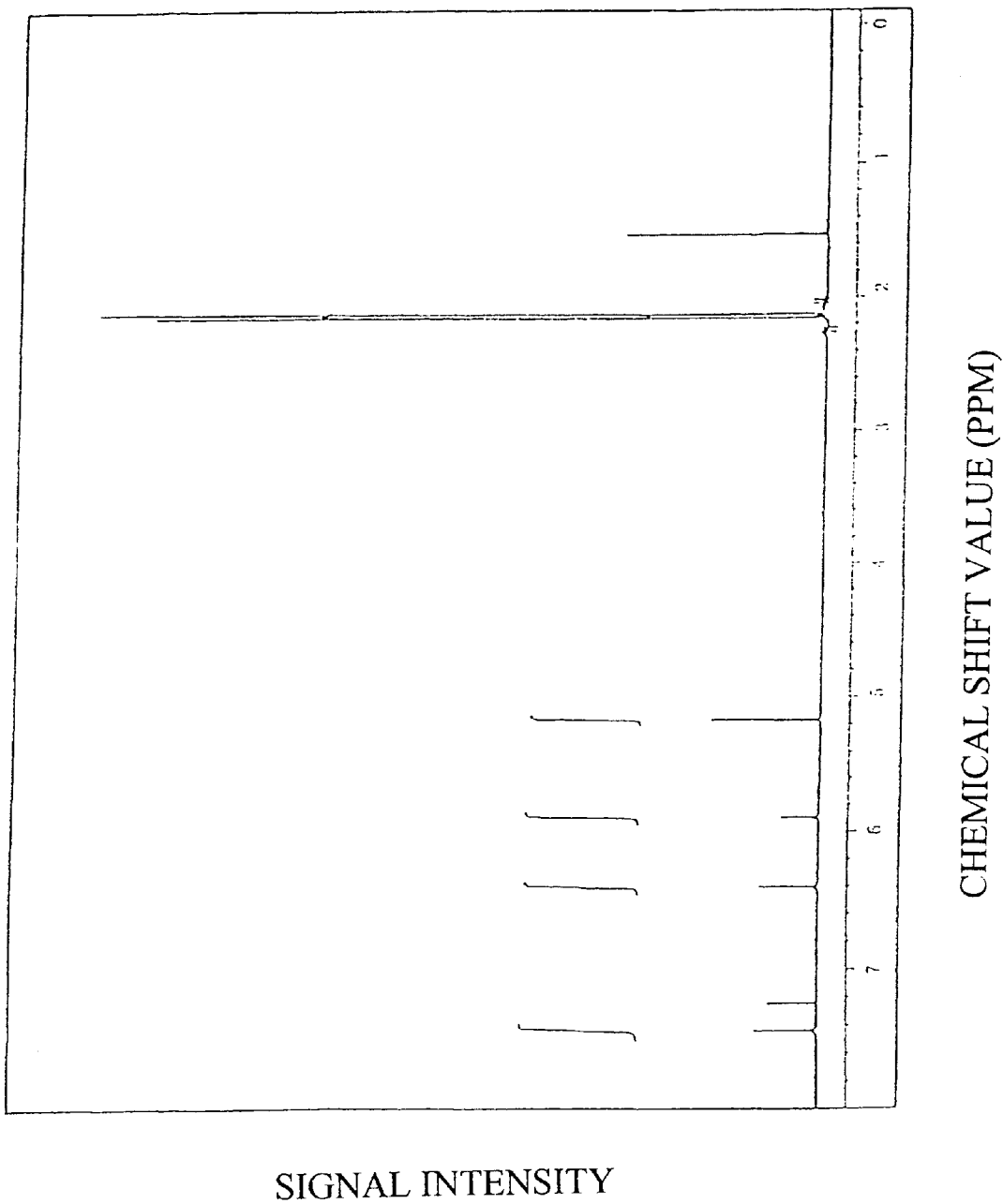
FIG. 2 shows a $^3$H-NMR spectrum of diacetylcyclopentenone.

FIG. 1 Shows a mass spectrum of diacetylcyclopentenone and FIG. 2 shows $^1$H-NMR spectrum of diacetylcyclopentenone. In FIG. 1, the abscissa indicates to the m/z value while the ordinate indicates to the relative intensity (%). In FIG. 2, the abscissa indicates to the chemical shift value (ppm) while the ordinate indicates to the signal intensity.

(3) The same reaction as in the above Example 1-(2) was conducted using 15.9 mg of the (−)-cyclopentenone obtained by the method of Example 1-(1) to give 15.1 mg of diacetyl (−)-cyclopentenone. This was subjected to a structural analysis by means of mass analysis and NMR by the same manner as in the above Example 1-(2) to give the same results as in the above 1-(2).

(4) The same reaction as in the above Example 1-(2) was conducted using 16.7 of the (+)-cyclopentenone obtained by the method of Example 1-(1) to give 18.8 mg of diacetyl (+)-cyclopentenone. This was subjected to a structural analysis by means of mass analysis and NMR by the same manner as in the above Example 1-(2) to give the same results as in the above 1-(2).

(5) To 13.8 mg of the cyclopentenone were added 44.3 mg of benzoic acid (041-20 manufactured by Nacalai Tesque), 7.5 mg of dimethylaminopyridine (DMAP; D1450 manufactured by Tokyo Kasei Kogyo) and 51.0 mg of N,N'-dicyclohexylcarbodiimide (DCC; 1001 manufactured by Peptide Kenkyusho), then 5 ml of chloroform was added thereto and the mixture was stirred for four hours with ice cooling. The reaction solution was filtered, the resulting filtrate was applied to 75 ml of a silica gel column and the column was eluted with chloroform to give a fraction containing dibenzoylcyclopentenone. The solvent of this fraction was evaporated in vacuo and the residue was dissolved in ethanol and separated by means of a silica gel thin layer chromatography using a 99:1 mixture of chloroform and methanol as a developing solvent. The silica gel corresponding to Rf=0.45~0.55 was scratched off from the thin layer followed by extracting with chloroform to give 3.2 mg of dibenzoylcyclopentenone.

Structural analysis of the resulting dibenzoylcyclopentenone by means of mass analysis and NMR was conducted by the same manner as in the above Example 1-(2). The result is given below.

MS m/z 323(M+H)$^+$ $^1$H-NMR

δ 5.56 (1H, d, J=3.0 Hz, H-5), 6.30 (1H, m, H-4), 6.54 (1H, d—d, J=1.5, 6.5 Hz, H-2), 7.44 (H of 4H, m, aromatic ring), 7.58 (H of 2H, m, aromatic ring), 7.64 (1H, d—d, J=2.0, 6.5 Hz, H-3), 8.06 (H of 4H, m, aromatic ring)

Figure 3:
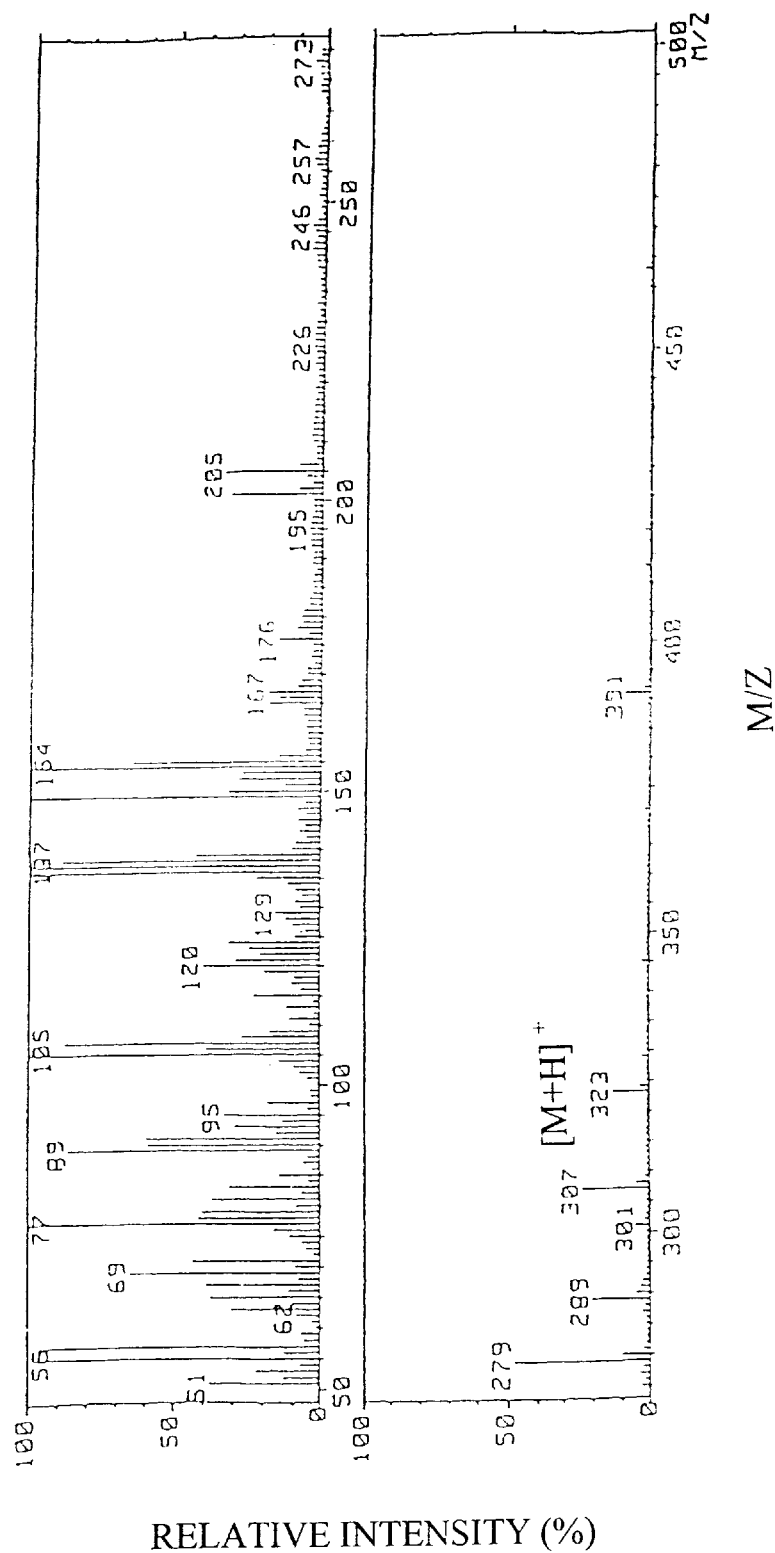
FIG. 3 shows a mass spectrum of dibenzoylcyclpentenone.
Figure 4:
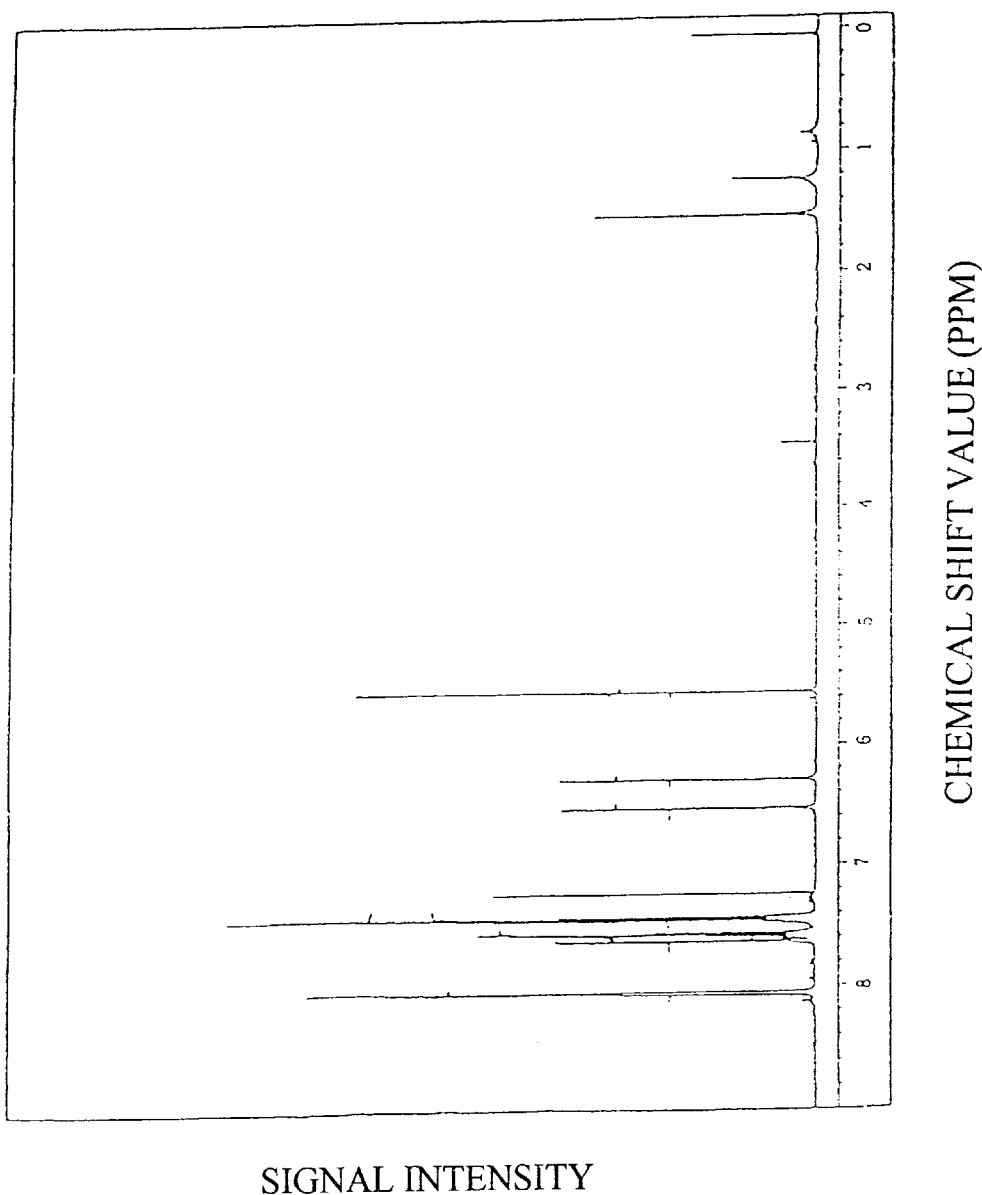
FIG. 4 shows a $^3$H-NMR spectrum of dibenzoylcyclopentenone.

FIG. 3 shows a mass spectrum of dibenzoylcyclopentenone and FIG. 4 shows $^1$H-NMR spectrum of dibenzoylcyclopentenone. In FIG. 3, the abscissa indicates to the m/z value while the ordinate indicates to the relative intensity (%). In FIG. 4, the abscissa indicates to the chemical shift value (ppm) while the ordinate indicates to the signal intensity.

(6) The same reaction as in the above Example 1-(5) was conducted using 22.1 mg of the (−)-cyclopentenone, 71.9 mg of benzoic acid, 12.1 mg of DMAP and 80.3 mg of DCC to give 19.2 mg of the dibenzoyl (−)-cyclopentenone. Structural analysis was conducted by means of mass analysis and NMR by the same manner as in the above Example 1-(5) and the same result as in Example 1-(5) was obtained.

(7) The same reaction as in the above Example 1-(5) was conducted using 20.4 mg of the (+)-cyclopentenone, 65.6 mg of benzoic acid, 11.0 mg of DMAP and 74.3 mg of DCC to give 21.4 mg of the dibenzoyl (+)-cyclopentenone. Structural analysis was conducted by means of mass analysis and NMR by the same manner as in the above Example 1-(5) and the same result as in Example 1-(5) was obtained.

(8) The cyclopentenone (30 mg), 10 mg of DMAP and 153 mg of hexanoic acid (070-26 manufactured by Nacalai Tesque) were dissolved in 5.9 ml of dichloromethane and then 108 mg of DCC was added thereto with ice cooling. After they were made to react for one hour, the reaction solution was separated and purified by means of a silica gel thin layer chromatography using chloroform as a developing solvent. The silica gel corresponding to Rf=0.3~0.4 was scratched off from the thin layer followed by extracting with chloroform to give 11 mg of dihexanoylcyclopentenone.

The resulting dihexanoylcyclopentenone was dissolved in $CDCl_3$ and confirmed by means of NMR. JNM-EX270 FT NMR system (manufactured by Nippon Denshi) was used as an apparatus for the NMR measurement. With regard to chemical shift values of $^1$H-NMR, the chemical shift value of tetramethylsilane was expressed as 0 ppm.

The result is given below.

$^1$H-NMR

δ 7.44 (1H, dd, $J_{2-3}$=6.27 Hz, $J_{3-4}$=1.98 Hz, H-3), 6.42 (1H, dd, $J_{2-3}$=6.27 Hz, $J_{3-4}$=1.32 Hz, H-2), 5.91 (1H, m, H-4), 5.16 (1H, d, $J_{4-5}$=2.97 Hz, H-5), 2.42 (2H, t, J=7.26 Hz), 2.38 (2H, t, J=7.76 Hz), 1.65 (4H, m), 1.26 (8H, m), 0.88 (6H, t)

Figure 5:
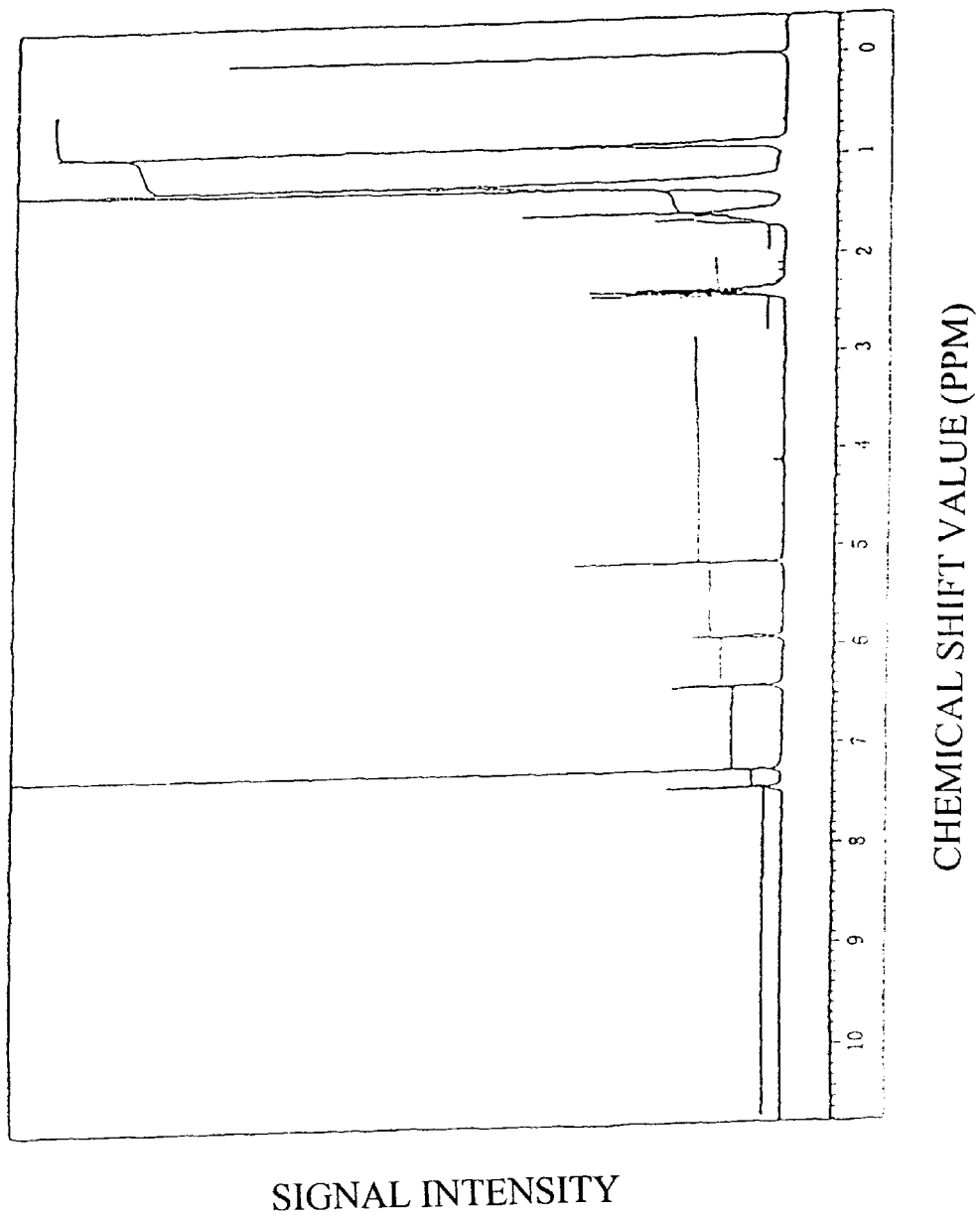
FIG. 5 shows a $^1$H-NMR spectrum of dihexanoylcyclopentenone.

FIG. 5 shows $^1$H-NMR spectrum of dihexanoylcyclopentenone. In FIG. 5, the abscissa indicates to the chemical shift value (ppm) while the ordinate indicates to the signal intensity.

(9) The cyclopentenone (30 mg), 10 mg of DMAP and 301 mg of myristic acid (M0476 manufactured by Tokyo Kasei Kogyo) were dissolved in 5.9 ml of dichloromethane and then 108 mg of DCC was added thereto with ice cooling. After they were made to react for one hour, the reaction solution was separated and purified by means of a silica gel thin layer chromatography using chloroform as a developing solvent. The silica gel corresponding to Rf=0.45~0.55 was scratched off from the thin layer followed by extracting with chloroform to give 53 mg of dimyristoylcyclopentenone.

Structural analysis of the resulting dimyristoylcyclopentenone by means of NMR was conducted by the same manner as in the Example 1(8). The result is given below.

$^1$H-NMR

δ 7.45 (1H, dd, $J_{2-3}$=5.94 Hz, $J_{3-4}$=2.31 Hz, H-3), 6.42 (1H, dd, $J_{2-3}$=5.31 Hz, $J_{3-4}$=1.32 Hz, H-2), 5.92 (1H, m, H-4), 5.16 (1H, d, $J_{4-5}$=2.64 Hz, H-5), 2.42 (2H, t, J=7.26 Hz), 2.38 (2H, t, J=7.91 Hz), 1.63 (4H, m), 1.26 (32H, m), 0.88 (6H, t)

Figure 6:
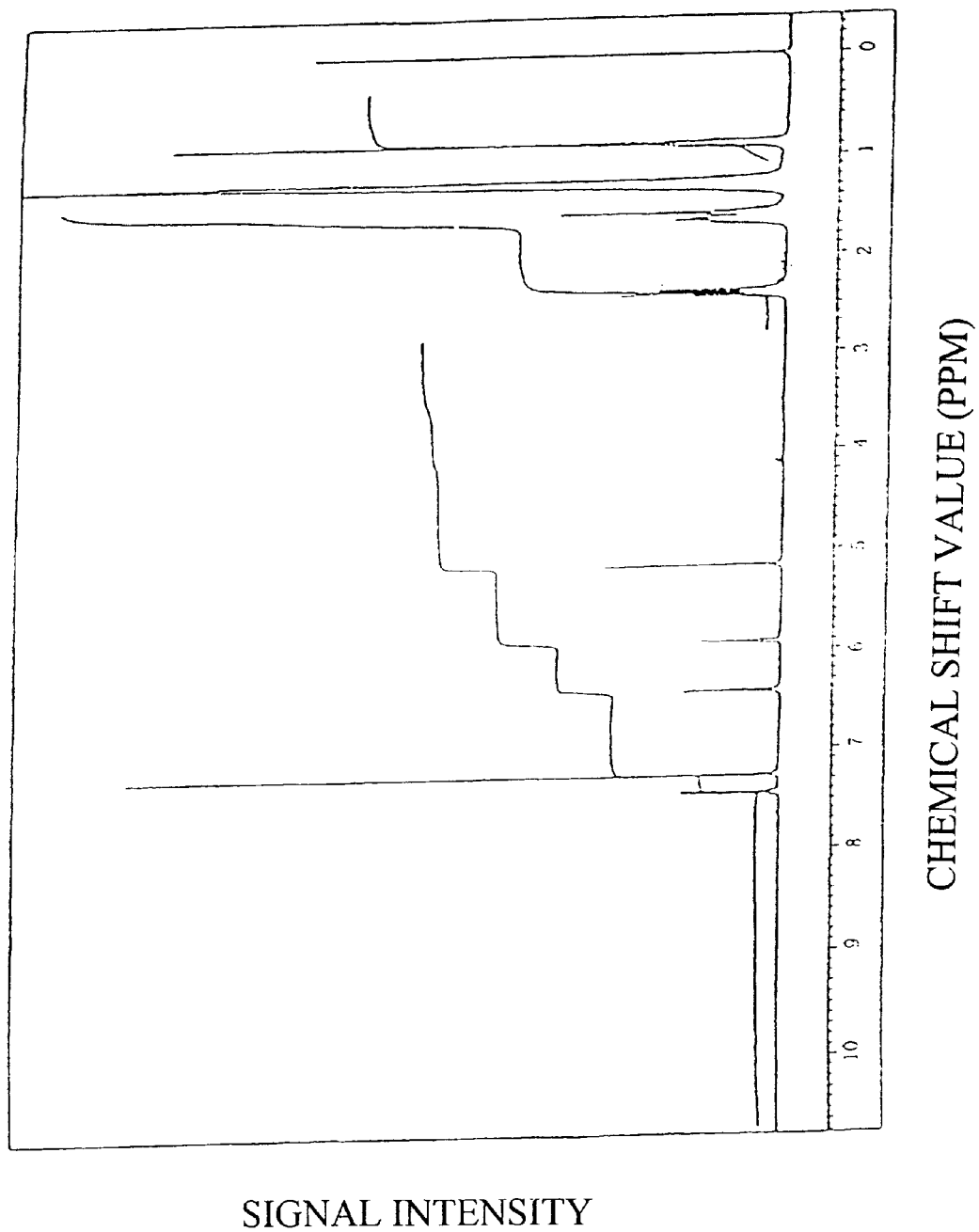
FIG. 6 shows a $^1$H-NMR spectrum of dimyristoylcyclopentenone.

FIG. 6 shows $^1$H-NMR spectrum of dimyristoylcyclopentenone. In FIG. 6, the abscissa indicates to the chemical shift value (ppm) while the ordinate indicates to the signal intensity.

(10) The cyclopentenone (30 mg), 10 mg of DMAP and 190 mg of octananoic acid (071-11 manufactured by Nacalai Tesque) were dissolved in 5.9 ml of dichloromethane and then 108 mg of DCC was added thereto with ice cooling. After they were made to react for one hour, the reaction solution was separated and purified by means of a silica gel thin layer chromatography using chloroform as a developing solvent. The silica gel corresponding to Rf=0.25~0.35 was scratched off from the thin layer followed by extracting with chloroform to give 27 mg of dioctanoylcyclopentenone.

Structural analysis of the resulting dioctanoylcyclopentenone by means of NMR was conducted by the same manner as in the Example 1-(8). The result is given below.

$^1$H-NMR

δ 7.44 (1H, dd, $J_{2-3}$=6.1 Hz, $J_{3-4}$=2.16 Hz, H-3), 6.41 (1H, dd, $J_{2-3}$=6.1 Hz, $J_{3-4}$=1.48 Hz, H-2), 5.92 (1H, m, H-4), 5.16 (1H, d, $J_{4-5}$=2.97 Hz, H-5), 2.42 (2H, t, J=7.59 Hz), 2.38 (2H, t, J=7.91 Hz), 1.65 (4H, m), 1.29 (16H, m), 0.88 (6H, t)

Figure 7:
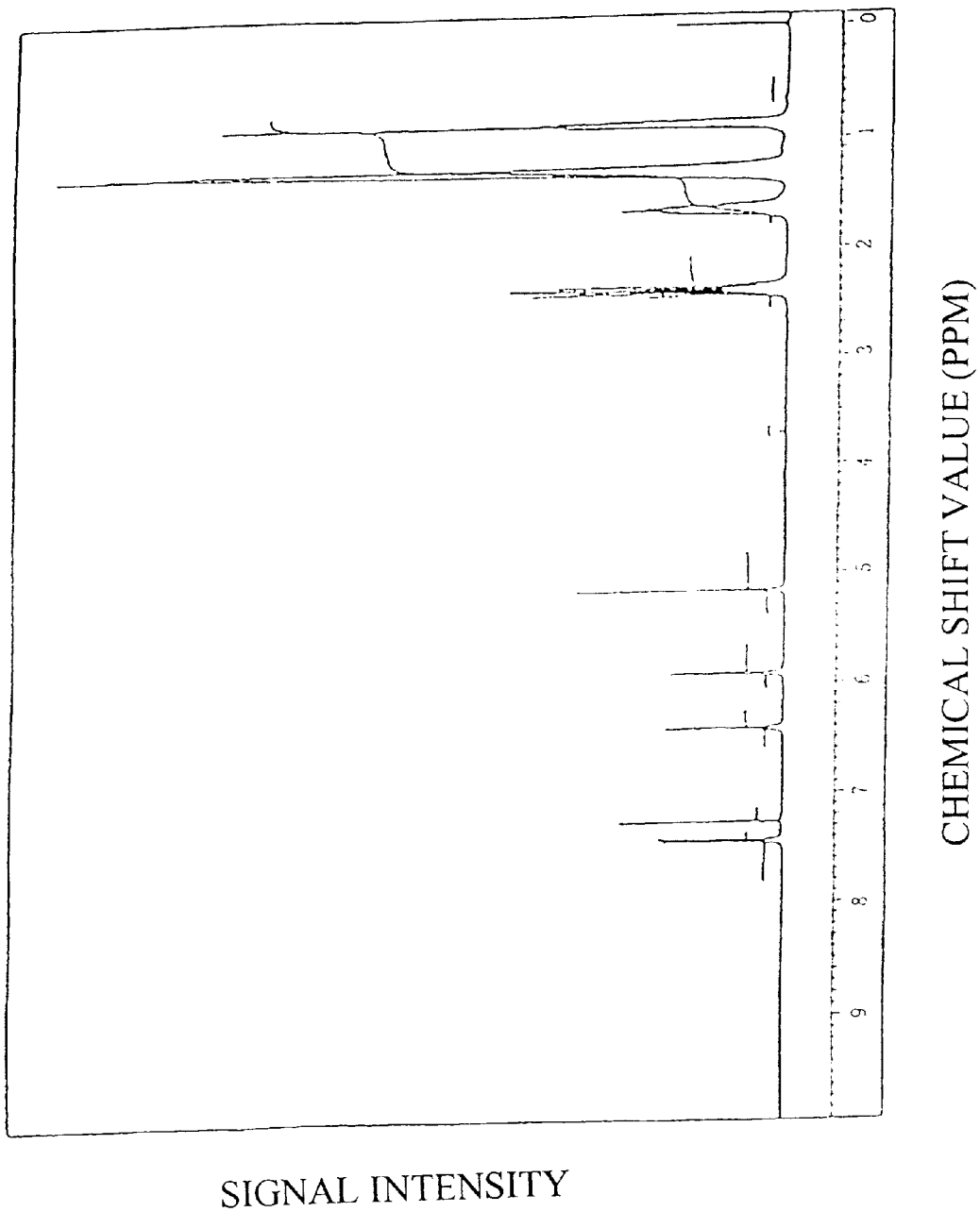
FIG. 7 shows a $^1$H-NMR spectrum of dioctanoylcyclopentenone.

FIG. 7 shows $^1$H-NMR spectrum of dioctanoylcyclopentenone. In FIG. 7, the abscissa indicates to the chemical shift value (ppm) while the ordinate indicates to the signal intensity.

(11) The cyclopentenone (30 mg), 10 mg of DMAP and 190 mg of 3-octenoic acid (00070 manufactured by Tokyo Kasei Kogyo) were dissolved in 5.9 ml of dichloromethane and then 108 mg of DCC was added thereto with ice cooling. After they were made to react for one hour, the reaction solution was separated and purified by means of a silica gel thin layer chromatography using chloroform as a developing solvent. The silica gel corresponding to Rf=0.25~0.35 was scratched off from the thin layer followed by extracting with chloroform to give 25 mg of di-3-octenoylcyclopentenone.

Structural analysis of the resulting di-3-octenoylcyclopentenone by means of NMR was conducted by the same manner as in the Example 1-(8). The result is given below.

$^1$H-NMR

δ 7.44 (1H, dd, $J_{2-3}$=6.27 Hz, $J_{3-4}$=2.32 Hz, H-3), 6.42 (1H, dd, $J_{2-3}$=6.27 Hz, $J_{3-4}$=1.49 Hz, H-2), 5.91 (1H, m, H-4), 5.55 (4H, m), 5.16 (1H, d, $J_{4-5}$=2.97 Hz, H-5), 3.12 (4H, dd, J=12.85 Hz, J=6.59 Hz), 2.04 (4H, m), 1.33 (8H, m), 0.89 (6H, t)

Figure 8:
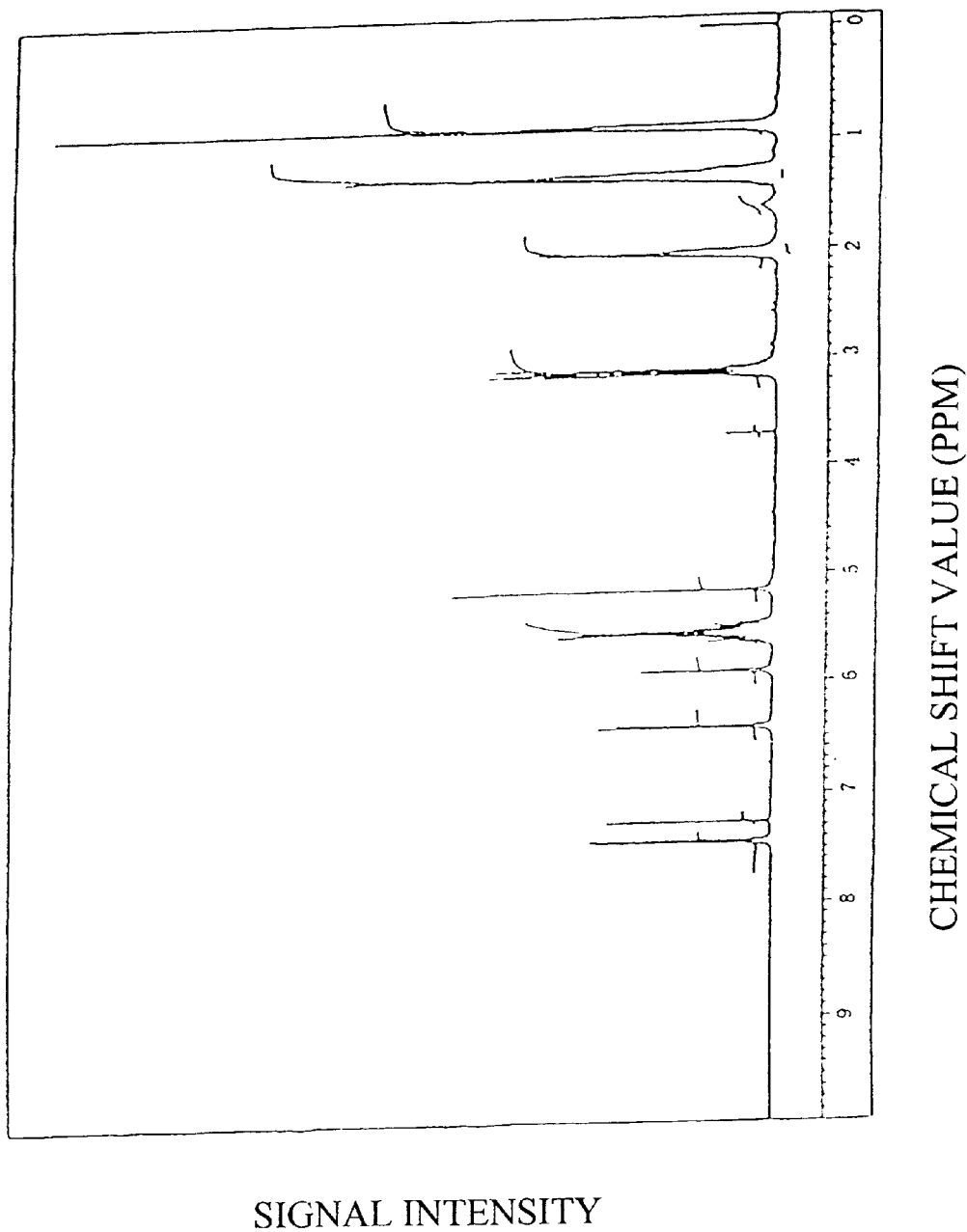
FIG. 8 shows a $^1$H-NMR spectrum of di-3-octenoylcyclopentenone.

FIG. 8 shows $^1$H-NMR spectrum of di-3-octenoylcyclopentenone. In FIG. 8, the abscissa indicates to the chemical shift value (ppm) while the ordinate indicates to the signal intensity.

(12) The cyclopentenone (30 mg), 10 mg of DMAP and 115 mg of n-butyric acid (B0754 manufactured by Tokyo Kasei Kogyo) were dissolved in 5.9 ml of dichloromethane and then 108 mg of DCC was added thereto with ice cooling. After they were made to react for one hour, the reaction solution was separated and purified by means of a silica gel thin layer chromatography using chloroform as a developing solvent. The silica gel corresponding to Rf=0.20~0.30 was scratched off from the thin layer followed by extracting with chloroform to give 16 mg of dibutyrylcyclopentenone.

Structural analysis of the resulting dibutyrylcyclopentenone by means of NMR was conducted by the same manner as in the Example 1-(8). The result is given below.

$^1$H-NMR

δ 7.45 (1H, dd, $J_{2-3}$=6.27 Hz, $J_{3-4}$=2.13 Hz, H-3), 6.42 (1H, dd, $J_{2-3}$=6.27 Hz, $J_{3-4}$=1.65 Hz, H-2), 5.91 (1H, m, H-4), 5.16 (1H, d, $J_{4-5}$=2.64 Hz, H-5)

Figure 9:
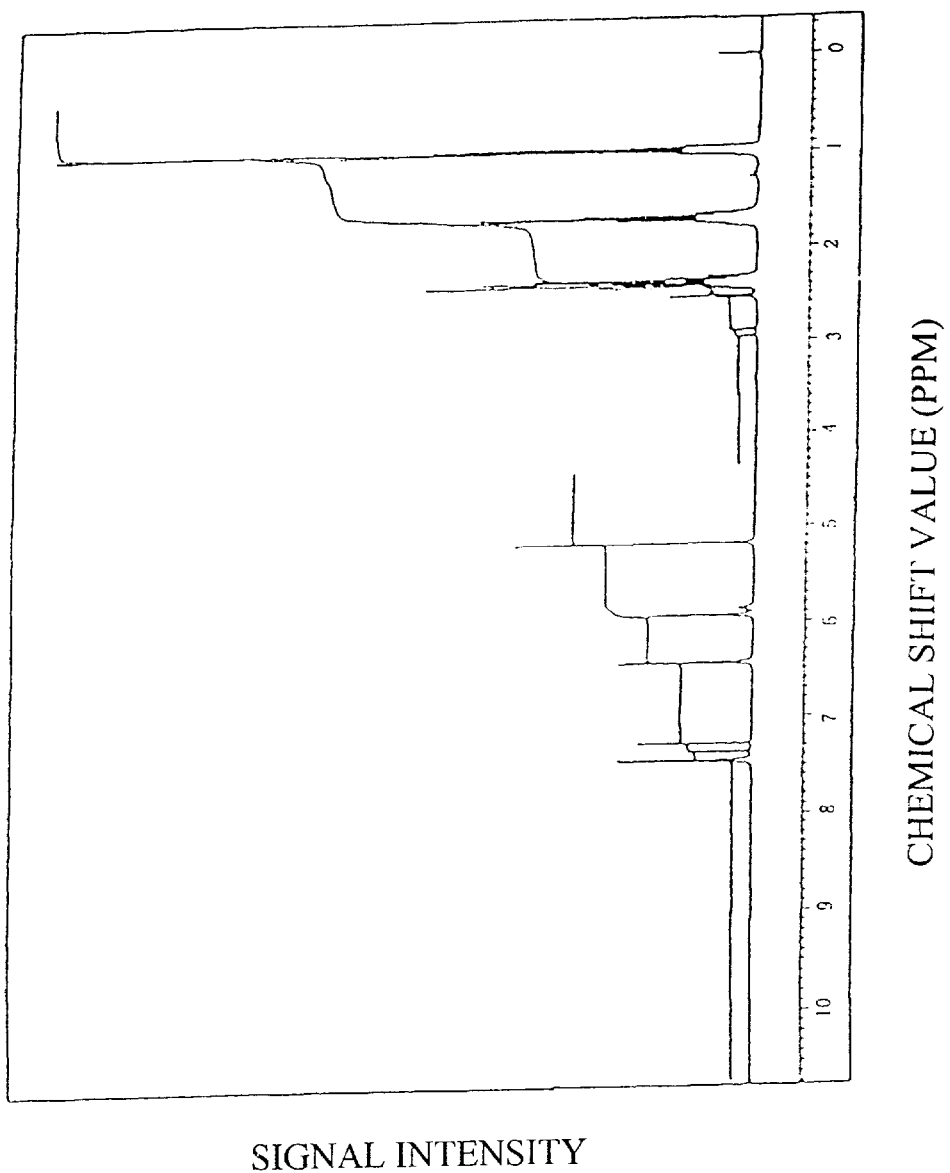
FIG. 9 shows a $^1$H-NMR spectrum of dibutyrylcyclopentenone.

FIG. 9 shows $^1$H-NMR spectrum of dibutyrylcyclopentenone. In FIG. 9, the abscissa indicates to the chemical shift value (ppm) while the ordinate indicates to the signal intensity.

(13) The cyclopentenone (30 mg), 10 mg of DMAP and 226 mg of n-decanoic acid (D0017 manufactured by Tokyo Kasei Kogyo) were dissolved in 5.9 ml of dichloromethane and then 108 mg of DCC was added thereto with ice cooling. After they were made to react for one hour, the reaction solution was separated and purified by means of a silica gel thin layer chromatography using chloroform as a developing solvent. The silica gel corresponding to Rf=0.35~0.45 was scratched off from the thin layer followed by extracting with chloroform to give 35 mg of didecanoylcyclopentenone.

Structural analysis of the resulting didecanoylcyclopentenone by means of NMR was conducted by the same manner as in the Example 1-(8). The result is given below.

$^1$H-NMR

δ 7.44 (1H, dd, $J_{2-3}$=6.27 Hz, $J_{3-4}$=1.97 Hz, H-3), 6.42 (1H, dd, $J_{2-3}$=6.27 Hz, $J_{3-4}$=1.3 Hz, H-2), 5.91 (1H, m, H-4), 5.15 (1H, d, $J_{4-5}$=2.97 Hz, H-5), 2.42 (2H, t, J=7.24 Hz), 2.38 (2H, t, J=7.91 Hz), 1.65 (4H, m), 1.26 (24H, m), 0.88 (6H, t)

Figure 10:
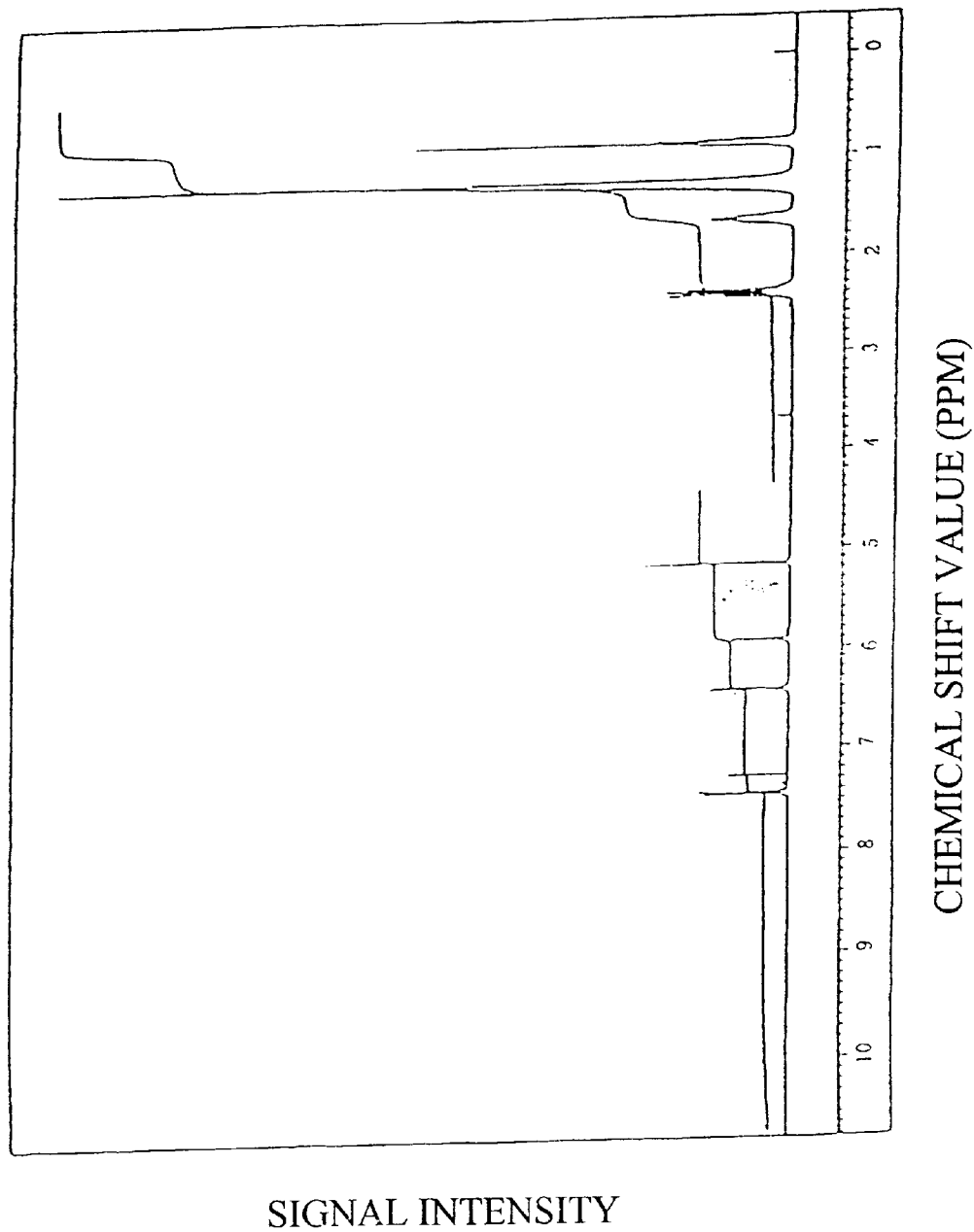
FIG. 10 shows a $^1$H-NMR spectrum of didecanoylcyclopentenone.

FIG. 10 shows $^1$H-NMR spectrum of didecanoylcyclopentenone. In FIG. 10, the abscissa indicates to the chemical shift value (ppm) while the ordinate indicates to the signal intensity.

(14) The cyclopentenone (30 mg), 16 mg of DMAP, 66 mg of triethylamine (T0424 manufactured by Tokyo Kasei Kogyo) and 122 mg of n-valeric anhydride (V0006 manufactured by Tokyo Kasei Kogyo) were dissolved in 5.9 ml of dichloromethane and the mixture was made to react with ice cooling for one hour. The reaction solution was developed by means of a silica gel thin layer chromatography using a 200:1 mixture of chloroform and methanol as a developing solvent and the silica gel corresponding to Rf=0.7~0.8 was scratched off from the thin layer and extracted with chloroform to give 39 mg of divalerylcyclopentenone.

Structural analysis of the resulting divalerylcyclopentenone by means of NMR was conducted by the same manner as in the Example 1-(8). The result is given below.

$^1$H-NMR

δ 7.45 (1H, dd, $J_{2-3}$=6.11 Hz, $J_{3-4}$=1.66 Hz, H-3), 6.42 (1H, dd, $J_{2-3}$=6.11 Hz, $J_{3-4}$=1.66 Hz, H-2), 5.91 (1H, m, H-4), 5.16 (1H, d, $J_{4-5}$=2.97 Hz, H-5), 2.43 (2H, dd, J=7.59, 7.59 Hz), 2.39 (2H, dd, J=7.59, 7.59 Hz), 1.65 (4H, m), 1.38 (4H, m), 0.93 (6H, dd, J=7.26, 7.26 Hz)

Figure 11:
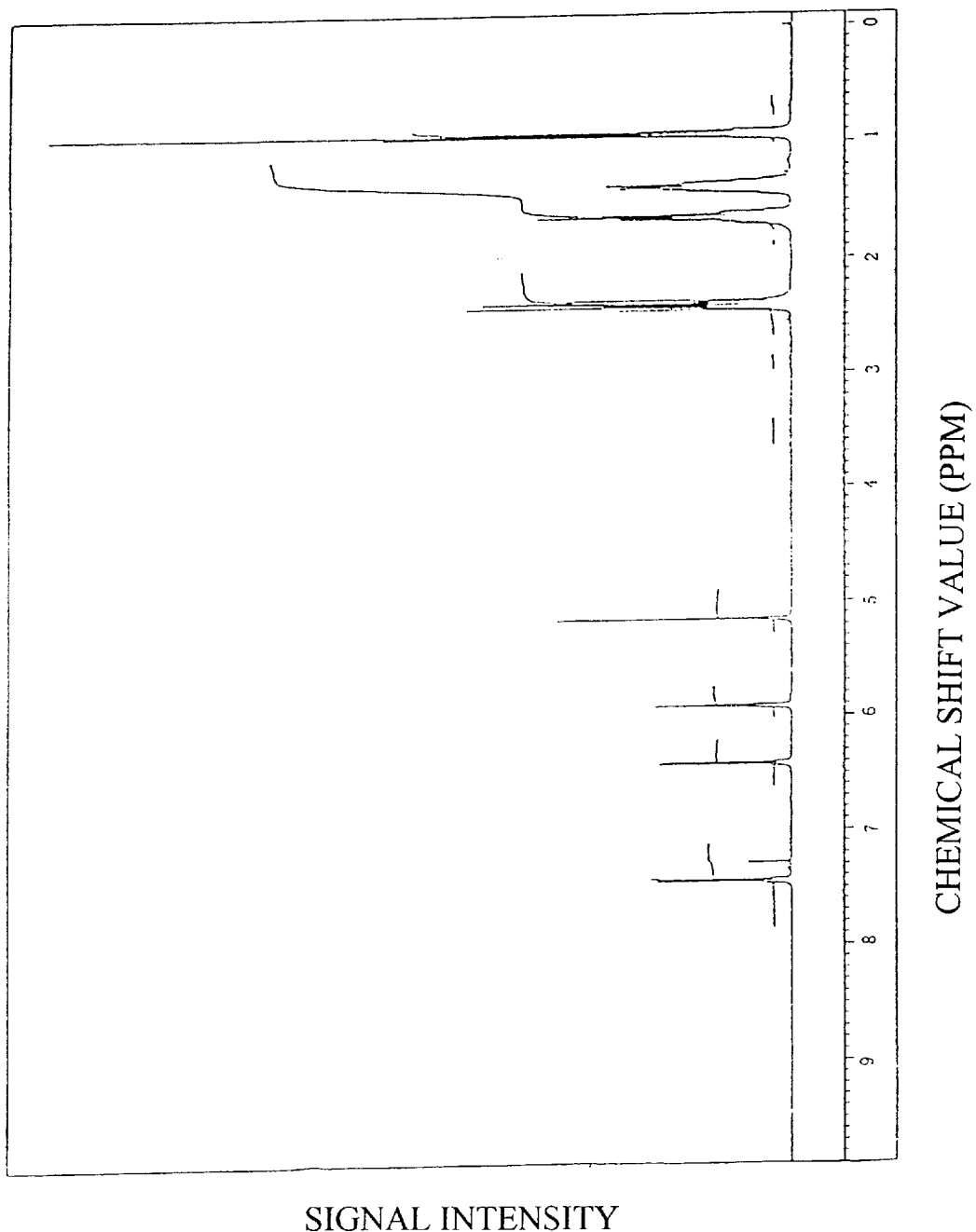
FIG. 11 shows a $^1$H-NMR spectrum of divalerylcyclopentenone.

FIG. 11 shows $^1$H-NMR spectrum of divalerylcyclopentenone. In FIG. 11, the abscissa indicates to the chemical shift value (ppm) while the ordinate indicates to the signal intensity.

(15) The cyclopentenone (30 mg), 16 mg of DMAP, 66 mg of triethylamine and 86 mg of propionic anhydride (P0513 manufactured by Tokyo Kasei Kogyo) were dissolved in 5.9 ml of dichloromethane and the mixture was made to react with ice cooling for one hour. The reaction solution was developed by means of a silica gel thin later chromatography using a 200:1 mixture of chloroform and methanol as a developing solvent and the silica gel corresponding to Rf=0.5~0.6 was scratched off from the thin layer and extracted with chloroform to give 31 mg of dipropionylcyclopentenone.

Structural analysis of the resulting dipropionylcyclopentenone by means of NMR was conducted by the same manner as in the Example 1-(8). The result is given below.

$^1$H-NMR

δ 7.45 (1H, dd, $J_{2-3}$=6.27 Hz, $J_{3-4}$=2.15 Hz, H-3), 6.42 (1H, dd, $J_{2-3}$=6.27 Hz, $J_{3-4}$=1.49 Hz, H-2), 5.91 (1H, m, H-4), 5.16 (1H, d, $J_{4-5}$=2.97 Hz, H-5), 2.46 (2H, dd, J=15.01, 7.59 Hz), 2.42 (2H, dd, J=15.01, 7.59 Hz), 1.18 (6H, dd, J=7.59, 7.59 Hz)

Figure 12:
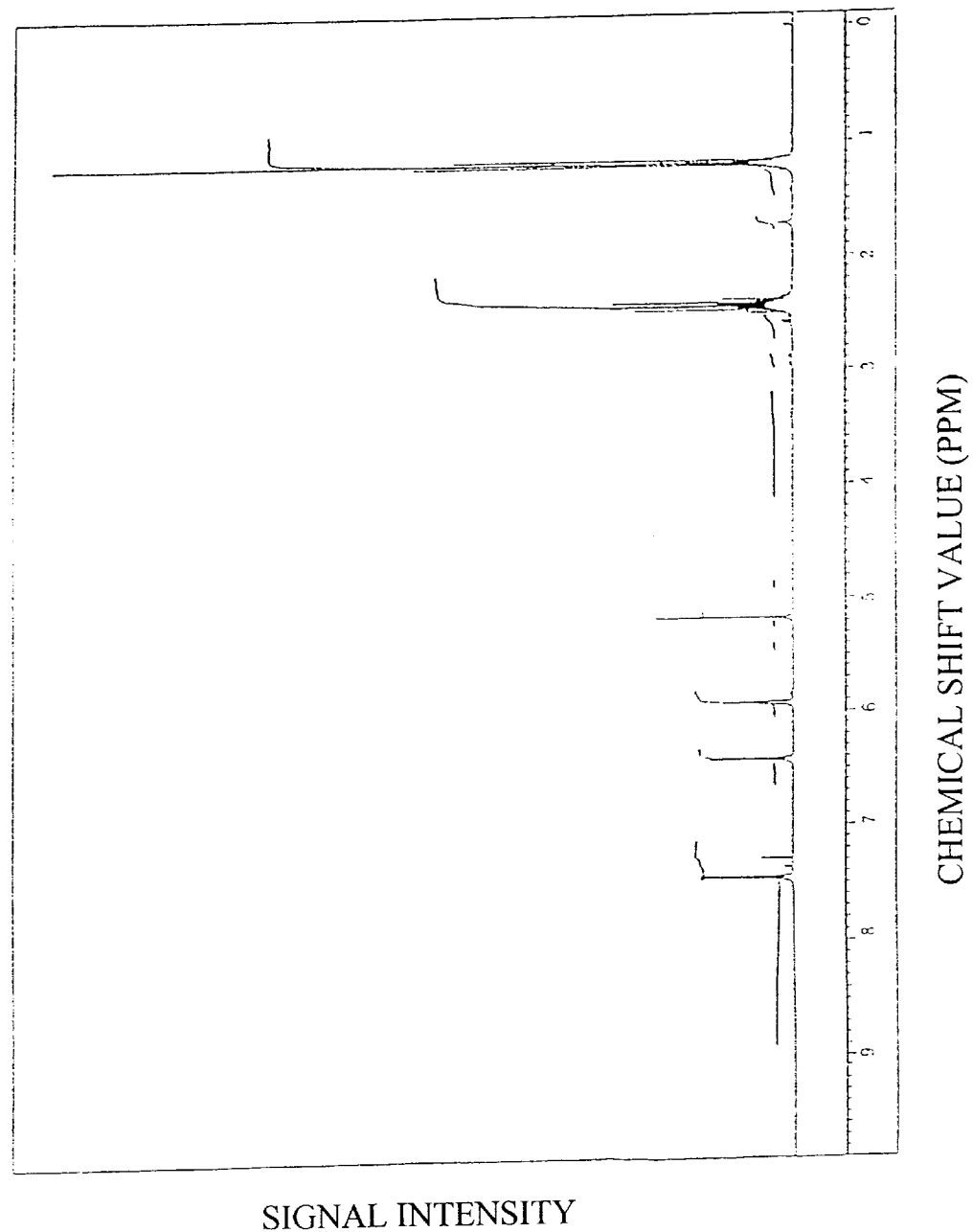
FIG. 12 shows a $^1$H-NMR spectrum of dipropionycyclopentenone.

FIG. 12 shows $^1$H-NMR spectrum of dipropionylcyclopentenone. In FIG. 12, the abscissa indicates to the chemical shift value (ppm) while the ordinate indicates to the signal intensity.

(16) The cyclopentenone (2 g), 733 mg of DMAP, 4.1 ml of trans-2-hexanoic acid (H0383 manufactured by Tokyo Kasei Kogyo) and 5.57 g of DCC were dissolved in 200 ml of dichloromethane and the mixture was made to react at room temperature for two hours. The reaction solution was subjected to a silica gel column chromatography using a 8:1 mixture of hexane and ethyl acetate as a solvent to give a fraction showing a single spot on a silica gel thin layer chromatography. This fraction was concentrated in vacuo to give about 900 mg of oily di-2-hexenoylcyclopenenone.

Structural analysis of the resulting di-2-hexenoylcyclopenenone by means of NMR was conducted by the same manner as in the Example 1-8). The result is given below.

$^1$H-NMR

δ 0.92 (6H, m, 11-H+11'-H), 1.48 (4H, m, 10-H+10'-H), 2.18 (4H, m, 9-H, 9'-H), 5.22 (1H, d, J=3.0 Hz, 5-H), 5.85 (2H, m, 7-H+7'-H), 5.98 (1H, m, 4-H), 6.41 (1H, dd, J=1.0, 6.0 Hz, 2 -H), 7.04 (2H, m, 8-H+8'-H), 7.47 (1H, dd, J=2.0, 6.0 Hz, 3-H)

Carbon atoms of the 2-hexenoyl group bonded to the position 5 of the cyclopentenone were named positions 6 to 11 from the carbonyl group successively while carbon atoms of the 2-hexenoyl group bonded to the position 4 of the cyclopentenone were named positions 6' to 11' from the carbonyl group successively.

Figure 13:
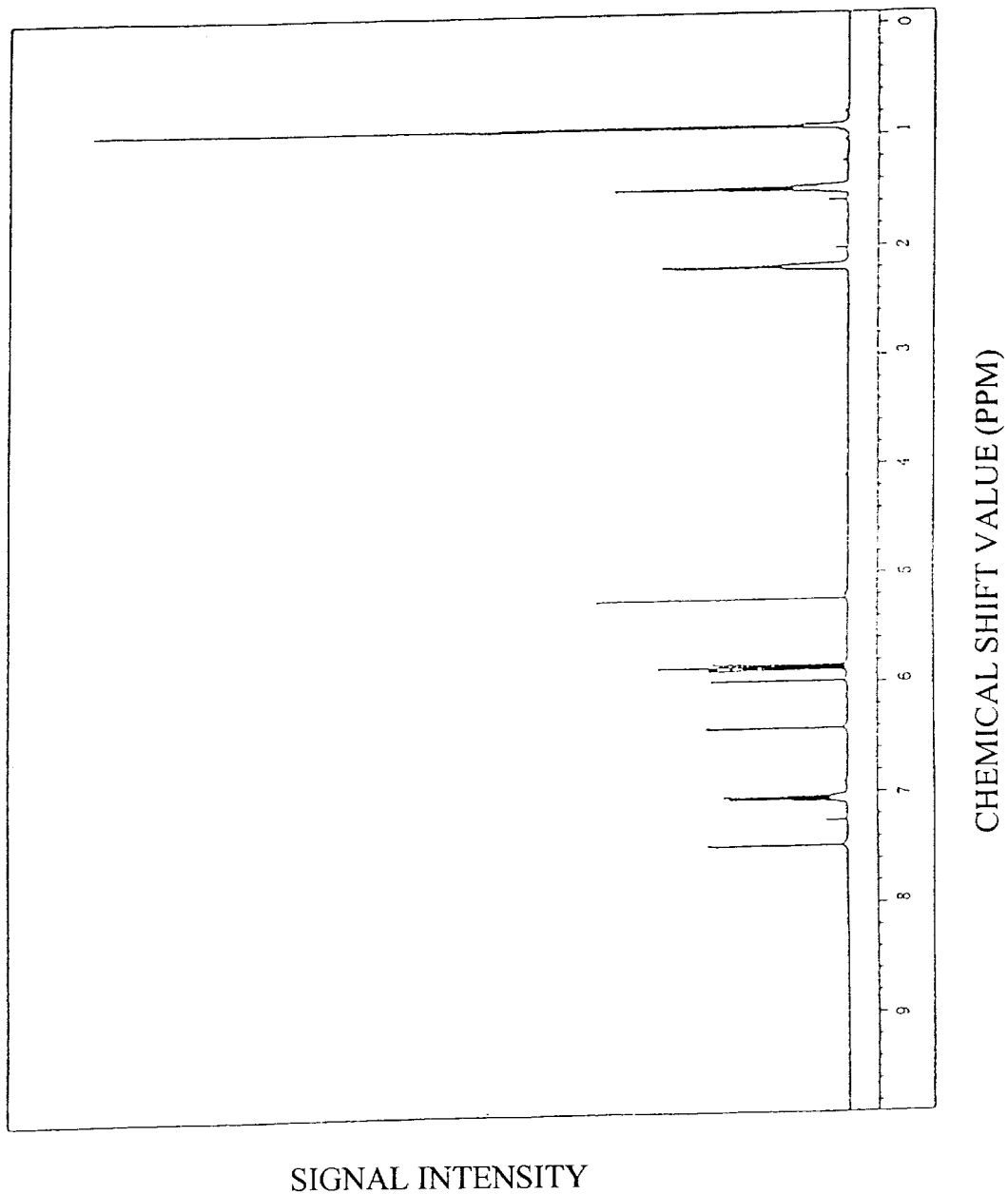
FIG. 13 shows a $^1$H-NMR spectrum of di-2-hexenoylcyclopentenone.

FIG. 13 shows $^1$H-NMR spectrum of di-2-hexenoylcyclopentenone. In FIG. 13, the abscissa indicates to the chemical shift value (ppm) while the ordinate indicates to the signal intensity.

EXAMPLE 2

(1). Each of 1 mM ethanolic solutions of diacetylcyclopentenone, diacetyl (−)-cyclopentenone, diacetyl (+)-cyclopentenone, dibenzoylcyclopentenone, dibenzoyl (−)-cyclopentenone, dibenzoyl (+)-cyclopenenone, dihexanoylcyclopentenone, dimyristoylcyclopentenone, dioctanoylcyclopentenone, di-3-octenoylcyclopentenone, dibutyrylcyclopentenone, didecanoylcyclopentenone, divalerylcyclopentenone, dipropionylcyclopentenone and di-2-hexenoylcyclopentenone was diluted with 70% aqueous solution of ethanol.

Each 5 µl of the diluted solutions was placed in a well of a 96-well microtiter plate and air-dried and then 100 µl of 10% fetal bovine serum-containing RPMI 1640 medium containing 5,000 HL-60 cells (ATCC CCL-240) was added to each well followed by incubating at 37° C. for 48 hours in the presence of 5% carbon dioxide gas. Shapes of the cells were observed under an optical microscope, 10 µl of phosphoric acid-buffered aqueous solution of sodium chloride containing 5 g/ml of 3-(4,5-dimethylthiazol-2-yl)-2, 5-diphenyltetrazolium bromide (MTT) was added thereto, the mixture was incubated for four hours more and the state of growth of the cells was observed under the microscope. Incidentally, 100 µl of 2-propanol containing 0.04 N HCl was added, the mixture was stirred well and the absorbance at 590 nm was measured and defined as the degree of growth of the cells. Minimum concentration of the cyclopentenone derivative contained in the well where living cells were not found was defined as the cell growth inhibiting concentration.

The result is given in Table 1.

TABLE 1

| Name of the Substance | Cell Growth Inhibiting Concentration (µM) |
| --- | --- |
| Diacetylcyclopentenone | 3.9 |
| Diacetyl(−)-cyclopentenone | 3.9 |
| Diacetyl(+)-cyclopentenone | 3.9 |
| Dibenzoylcyclopentenone | 7.7 |
| Dibenzoyl(−)-cyclopentenone | 7.7 |
| Dibenzoyl(+)-cyclopentenone | 7.7 |
| Dihexanoylcyclopentenone | 3.0 |
| Dimyristoylcyclopentenone | 187 |
| Dioctanoylcyclopentenone | 9.8 |
| Di-3-octenoylcyclopentenone | 5.0 |
| Dibutyrylcyclopentenone | 3.4 |
| Didecanoylcyclopentenone | 17.2 |
| Divalerylcyclopentenone | 6.2 |
| Dipropionylcyclopentenone | 3.8 |
| Di-2-hexenoylcyclopentenone | 6.2 |

In each of the cell growth inhibiting concentrations, apoptic bodies were produced in the cells. Incidentally, optically active substances of those compounds showed similar cell growth inhibiting action and apoptosis inducing actions as well.

EXAMPLE 3

Staphylococcus aureus 3A (NCTC 8319; test microbe (1)), Bacillus subtilis IFO 3021 (test microbe (2)) and Pseudomonas aeruginosa IFO 3081 (test microbe (3)) were incubated overnight in a sensitive bouillon medium (manufactured by Nissui) (seed culture). The absorbance at 600 nm was measured and the numbers of the living cells were calculated from a calibration curve showing the relation between the numbers of living cells and the absorbance at 600 nm. The incubated liquid was diluted with a fresh sensitive bouillon medium to an extent of 1×10$^6$ cells/ml and then each 180 µl was placed into each well of the 96-well microtiter plate. Each 20 µl of aqueous solutions of 2,000 µg/ml, 1,000 µg/ml, 500 µg/ml, 250 µl/ml, 125 µl/ml and 62.5 µl/ml dihexanoylcyclopentenone obtained in Example 1-(8) or water was placed into each of the wells and a stationary culture was conducted overnight at 37° C. (main culture). In the meanwhile, a part of the seed culture liquid was diluted with sterilized water, applied onto a sensitive bouillon agar plate medium and incubated overnight at 37° C. and numbers of the colonies were counted to measure the precise numbers of the living cells.

The incubated liquid of each well after the main culture was diluted with sterilized water, applied onto a sensitive bouillon agar plate medium and incubated overnight at 37° C. and numbers of the colonies were counted to measure the numbers of the living cells.

Minimum concentration where the numbers of the living cells are smaller as compared with the well to which water was added was defined as the growth inhibiting concentration while the minimum concentration where the numbers of the living cells are smaller as compared with the initial stage of the main culture was defined as the sterilizing concentration. The results are given in Table 2.

Data in Table 2 are the concentrations of dihexanoylcyclopentenone showing the growth inhibiting action and the sterilizing action to the test microbes (1)~(3) and the unit is μg/ml.

TABLE 2

|  | Growth Inhibiting Concentration | Sterilizing Concentration |
| --- | --- | --- |
| Test Microbe (1) | 100 | 100 |
| Test Microbe (2) | 100 | 100 |
| Test Microbe (3) | 200 | 200 |

It is apparent from the above results that dihexanoylcyclopentenone has a potent antibacterial activity. Other compounds prepared in Example 1 and optically active substances thereof also showed the same antibacterial activity as dihexanoylcyclopentenone.

EXAMPLE 4

Injection Preparations (1) Diacetylcyclopentenone or dihexanoylcyclopentenone was added to a physiological saline solution (the same as above) in a concentration of 1% to prepare an injection preparation.

(2) Dibenzoylcyclopentenone or dibutyrylcyclopentenone, and glycyrrhizic acid were added to a physiological saline solution (the same as above) in concentrations of 0.5% and 0.1%, respectively, to prepare an injection preparation.

EXAMPLE 5

Tablets (1) A tablet containing 100 mg of dibenzoylcyclopentenone and an appropriate amount of microcrystalline cellulose was prepared and coated with sugar to manufacture a tablet preparation.

(2) A tablet containing 0.1 mg of diacetyl(−)-cyclopentenone, 10 mg of dipotassium glycyrrhizinate and an appropriate amount of microcrystalline cellulose was prepared and coated with sugar to manufacture a tablet preparation.

MERIT OF THE INVENTION

The present invention offers the manufacturing method for the cyclopentenone derivative, an optically active substance thereof or a salt thereof which exhibits the physiological activities such as anticancer activity, cell growth inhibiting activity on cancer cells, apoptosis induction activity, antibacterial activity, etc. The pharmaceutical agent using the compound obtained by the present invention as an effective component is a useful pharmaceutical agent especially for keeping homeostatis of living body.

What is claimed is:

1. A cyclopentenone derivative represented by the following formula or an optically active substance or a salt thereof,

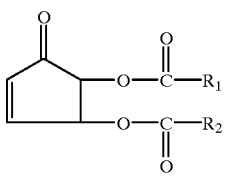

(In the formula, $R_1$ and $R_2$ are same or different and each of them is straight or branched alkyl group, straight or branched alkenyl group, aromatic group or aromatic-aliphatic group with a proviso that the case where $R_1=R_2=-CH_3$ is excluded).

2. A pharmaceutical agent which is characterized in containing at least one compound selected from the cyclopentenone derivative, an optically active substance or a salt thereof according to claim 1 as an effective component.

3. A pharmaceutical agent according to claim 2 which the agent is an anticancer agent.

4. A pharmaceutical agent according to claim 2 which the agent is an apoptosis-inducing agent.

5. A pharmaceutical agent according to claim 2 which the agent is an antibacterial agent.

6. A pharmaceutical agent which is characterized in containing at least one compound selected from the cyclopentenone derivative, an optically active substance or a salt thereof obtained by the following method as an effective component;

wherein a method for the manufacture of a cyclopentenone derivative represented by the formula II, characterized in that, 4,5-dihydroxy-2-cyclopenten-1-one represented by the following formula III and/or an optically active derivative thereof are/is made to react with a carboxylic acid and/or a reactive derivative thereof corresponding to $R_3$ and $R_4$ of the cyclopentenone derivative represented by the following formula II either simultaneously or successively;

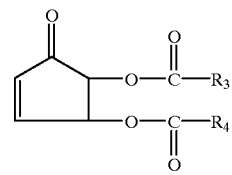

wherein $R_3$ and $R_4$ are same or different and each of them is a straight or branched alkyl group, a straight or branched alkenyl group, an aromatic group or an aromatic-aliphatic group, with a proviso that the case where $R_1=R_2=CH_3$ is excluded.

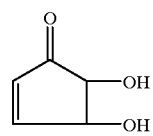

7. A pharmaceutical agent according to claim 6 which the agent is an anticancer agent.

8. A pharmaceutical agent according to claim 6 which the agent is an apoptosis-inducing agent.

9. A pharmaceutical agent according to claim 6 which the agent is an antibacterial agent.

* * * * *

UNITED STATES PATENT AND TRADEMARK OFFICE
CERTIFICATE OF CORRECTION

PATENT NO.     : 6,136,854
DATED          : October 24, 2000
INVENTOR(S)    : Nobuto Koyama et al.

Page 1 of 1

It is certified that error appears in the above-identified patent and that said Letters Patent is hereby corrected as shown below:

<u>Title page,</u>
Item [30] Foreign Application Priority Data,
Mar. 11, 1997   [JP]   Japan ................... 9-72855
Mar. 26, 1997   [JP]   Japan ................... 9-90011

Signed and Sealed this

Twelfth Day of February, 2002

Attest:

JAMES E. ROGAN
Attesting Officer                Director of the United States Patent and Trademark Office